US006617163B1

(12) United States Patent
Grosjean-Cournoyer et al.

(10) Patent No.: US 6,617,163 B1
(45) Date of Patent: Sep. 9, 2003

(54) POLYNUCLEOTIDES FOR MUTAGENESIS IN FUNGUS COMPRISING A FUNCTIONAL GENE IN MAGNAPORTHE AND AN IMPALA TRANSPOSON

(75) Inventors: Marie-Claire Grosjean-Cournoyer, Caluire (FR); Francois Villalba, Lyons (FR); Marc-Henri Lebrun, Lyons (FR); Marie-Josee Daboussi, Bures-sur-Yvette (FR)

(73) Assignee: Aventis Cropscience S.A., Lyons (FR)

( * ) Notice: Subject to any disclaimer, the term of this patent is extended or adjusted under 35 U.S.C. 154(b) by 0 days.

(21) Appl. No.: 09/937,236

(22) PCT Filed: Mar. 22, 2000

(86) PCT No.: PCT/FR00/00713

§ 371 (c)(1), (2), (4) Date: Dec. 26, 2001

(87) PCT Pub. No.: WO00/56902

PCT Pub. Date: Sep. 28, 2000

(30) Foreign Application Priority Data

Mar. 22, 1999 (FR) .......................................... 99 03701

(51) Int. Cl.[7] .......................... C12N 15/74; C12N 1/00; C12N 1/14

(52) U.S. Cl. ....................... 435/473; 435/440; 435/471; 435/476; 435/477; 435/480; 435/481; 435/243; 435/254.1; 435/254.11; 435/254.3; 435/254.5; 435/254.7; 435/320.1; 536/23.1; 536/24.1

(58) Field of Search ................................ 435/440, 471, 435/473, 476, 479, 480, 481, 243, 254.1, 254.11, 254.3, 254.5, 254.7, 320.1; 536/22.1, 23.1, 24.1

(56) References Cited

U.S. PATENT DOCUMENTS 5,595,889 A * 1/1997 Richaud et al. ............ 435/71.2
5,985,570 A * 11/1999 Amutan et al. ................ 435/6

OTHER PUBLICATIONS

Punt et al. A twin reporter vector for simultaneous analysis of expression signals of divergently transcribed, contiguous genes in filamentous fungi. Gene 104: 119–122, 1991.*

Balhadere PV, Talbot NJ. PDE1 encodes a P–type ATPase involved in appressorium–mediated plant infection by the rice blast fungus *Magnaporthe grisea.* Plant Cell Sep. 2001;13(9):1987–2004.

Ikeda K, Nakayashiki H, Takagi M, Tosa Y, Mayama S. Heat shock, copper sulfate and oxidativ stress activate the retrotransposon MAGGY resident in the plant pathogenic fungus *Magnaporth grisea.* Mol Genet Genomics 2001;266:318–325.

Kang S, Lebrun MH, Farrall L, Valent B. Gain of virulence caused by insertion of a Pot transposon in a *Magnaporthe grisea* avirulence gene. Mol Plant Microbe Interact 200 May;14(5):671–674.

Liu ZM, Kolattukudy PE. Early expression of the calmodulin gene, which precedes appressorium formation in *Magnaporthe grisea,* is inhibited by self–inhibitors and requires surface attachmen J Bacteriol Jun. 1999; 181(11):3571–3577.

Urban M, Bhargava, T, Hamer JE. An ATP–driven efflux pump is a novel patogenicity factor in rice blast disease. EMBO J Feb. 1, 1999; 18(3):512–521.

Lauge R, De Wit PJ. Fungal avirulence genes: structure and possible functions. Fungal Genet Biol Aug. 1998;24(3):285–297.

Xu JR, Hamer JE. MAP kinase and cAMP signaling regulate infection structure formation and pathogenic growth in the rice blast fungus *Magnaporthe grisea.* Genes Dev 1996 No. 1;10(21):2696–706.

Kang S, Sweigard JA, Valent B. The PWL host specificity gene family in the blast fungus *Magnaporthe grisea.* Mol Plant Microbe Interact Nov.–Dec. 1995;8(6):939–948.

Lebrun M–H, Chumley F, Valent B. Molecular analysis of spontaneous mutations in *Magnaporthe grisea.* Fungal Genetics News Letter 1994;41 A:52.

Talbot NJ, Ebbole DJ, Hamer JE. Identification and characterization of MPG1, a gene involved in pathogenicity from the rice blast fungus *Magnaporthe grisea.* Plant Cell Nov. 1993;5(11):1575–1590.

Langin et al., "Influence of biological parameters and gene transfer technique on transformation of *Fusarium oxysporum*", Current Genetics (1990) 17:313–319.

Durand et al., "Transformation of *Penicillium roqueforti* to phleomycin– and to hygromycin B–resistance", Current Genetics (1991) 19:149–153.

Dobinson et al., "The ebb and flow of a fungal genome", Trends in Microbiology 348, vol. 1 No. 9, Dec. 1993.

Kachroo et al., "Pot2, an inverted repeat transposon from the rice blast fungus *Magnaporthe grisea*", Mol Gen Genet (1994) 245:339–348.

Daboussi et al., "Transposable elements in the fungal plant pathogen *Fusarium oxysporum*", Genetica 93:49–59, 1994.

Langin et al., "The transposable element *impala,* a fungal member of the *Tc1–mariner* superfamily", Mol Gen Genet (1995) 246:19–28.

Farman et al., "The *Magnaporthe grisea* DNA fingerprinting probe MGR586 contains the 3' end o an inverted repeat transponson", Mol Gen Genet (1996) 251:675–681.

Daboussi, "Fungal transposable elements: generators of diversity and genetic tools", J. Genet, vol. 75, No. 3, Dec. 1996, pp. 325–339.

Kachroo et al., "Organisation and molecular analysis of repeated DNA sequences in the rice blast fungus *Magnaporthe grisea*", Curr Genet (1997) 31:361–369.

Hua–Van et al., "Three highly divergent subfamilies of the *impala* transposable element coexist in the genome of the fungus *Fusarium oxysporum*", Mol Gen Genet (1998) 259: 354–362.

Brown et al., "Insertional mutagensis of pathogenic fungi", (1998) 390–394; XP–000856194.

* cited by examiner

*Primary Examiner*—David Guzo
*Assistant Examiner*—David A. Lambertson
(74) *Attorney, Agent, or Firm*—Baker Botts L.L.P.

(57) ABSTRACT

The invention concerns a new tool for efficient mutagenesis enabling the generation of a collection of mutants in fungi by random insertion of a characterized *Fusarium oxysporum* Impala transposon in the genome of said fungi. The invention also concerns the resulting mutants.

18 Claims, 14 Drawing Sheets

POLYNUCLEOTIDES FOR MUTAGENESIS IN FUNGUS COMPRISING A FUNCTIONAL GENE IN MAGNAPORTHE AND AN IMPALA TRANSPOSON

The present invention relates to novel polynucleotides, and to the use of these polynucleotides, for insertional mutagenesis and gene tagging in fungi. The invention also relates to collections of fungus mutants obtained by random insertion of the Impala transposon from *Fusarium oxysporum* into the genome of these fungi. These collections of mutants represent an effective genetic tool for studying the function of genes in fungi.

Transposons may be defined as mobile genetic elements capable of moving between two DNA sequences. By virtue of their capacity to insert into genes (exons, introns, regulatory regions), they can be the cause of mutations. Because of this, they contribute to the evolution of the genomes in which they exist as a parasite. Transposons have been classified in two groups depending on their propagation method (Finnegan, 1989; Capy et al., 1998):

Class I elements (retroelements) transpose via an RNA intermediate which is reverse-transcribed into DNA by a reverse transcriptase. This class is subdivided into retroelements or retrotransposons which may or may not be bordered by LTRs (long terminal repeats). Among the LTR retroelements are the elements of the gypsy family and of the copia family. They have genes which are homologous to the gag and pol genes of retroviruses and differ in the organization of the various functional domains of the pol gene. In addition, the gypsy family has a gene which is homologous to env which, in retroviruses, contributes to their infectiousness. Among the non-LTR retroelements LINEs which have gag and pol genes and a poly-A sequence are distinguished, and also SINEs, which also have a poly-A tail but lack gag and pol sequences, are distinguished; they are presumed to derive from prior LINE elements (Eickbush, 1992; Okada and Hamada, 1997);

Class II elements transpose via a mechanism of excision and reinsertion of the transposon DNA sequence. Their general structure consists of two inverted repeat sequences (ITRs) bordering an open reading frame encoding a transposase required for the transposition of the element. These elements have been grouped together into superfamilies, according to the sequence homologies of their transposases and/or of the ITRs, including that of the Tc1/mariner elements (Doak et al., 1994), of the Fot1/Pogo elements (Capy et al., 1998; Smit and Riggs, 1996), of the hAT elements (Calvi et al., 1991), of the P elements (Kidwell, 1994) or of the CACTA elements (Gierl 1996).

The identification and study of fungus transposons is of very great value, in particular with a view to developing tools for insertional mutagenesis (Brown et al., Curr. Opin. Microbiol. 1:390–4, 1998) and also for studying the genome of these fungi (Dobinson et al., Trends in Microbiology, 1:348–3652, 1993).

Various strategies have therefore been implemented for identifying transposons in the genome of fungi. The first and second take advantage of the knowledge which derives from previously characterized elements. This involves the use of heterologous probes used in Southern hybridization experiments or amplifications using oligonucleotides derived from highly conserved domains, such as that of the LTR retroelement reverse transcriptase. The third strategy consists in characterizing repeat DNA sequences. In this case, differential hybridization between the genomic DNA and a ribosomal probe is required. Transposons of the Fot1 family have thus been identified in the *Magnaporthe grisea* genome (Kachroo et al., Current Genetics 31:361–369, 1997; Farman et al., Mol. Gen. Genetics 251:675–681 1996; Kachroo et al., Mol. Gen. Genetics 245:339–348, 1994). The final method, unlike the previous three, makes it possible to identify functional and active elements; this is the transposon trap. This strategy uses the inactivation of a marker gene in which the mutation engendered by the insertion of the element can be identified using a positive screen. Thus, the am (glutamate dehydrogenase) gene has made it possible to characterize the Tad retroelement, which is of the LINE type, in *Neurospora crassa*, following its reinsertion into this gene (Kinsey and Helber, 1989). The niaD (nitrate reductase) gene of *Aspergillus nidulans* has also been used for trapping transposons. Specifically, a mutation which inactivates this gene confers chlorate resistance. Various transposons have thus been identified in *Fusarium oxysporum* (Daboussi et al., Genetica 93:49–59, 1994) and in Aspergillus (U.S. Pat. No. 5,985,570). The class II element Fot1 from *Fusarium oxysporum* was the first transposon identified using inactivation of the niaD gene (Daboussi et al., 1992). In addition, the use of the niaD gene in *Fusarium oxysporum* has made it possible to trap the Impala transposon belonging to the superfamily of the Tc1/mariner-type elements (Langin et al., 1995). Various Impala transposon subfamilies have been identified in *Fusarium oxysporum* (Hua-Van et al., Mol. Gen. Genetics 259:354–362, 1998). The transposition of the Impala element has been studied in *Fusarium oxysporum*. When the Impala transposon is integrated into the promoter or the introns of a given gene, it may then inactivate the expression of this gene. On the other hand, after transposition of the Impala transposon, the gene is reactivated, which constitutes a positive control for the transposition event. Such a strategy for identifying the transposition has been used in Fusarium with a construct comprising the Impala transposon integrated into the promoter regulatory sequence of the nitrate reductase (niaD) gene from *Aspergillus nidulans* (Hua-Van, 1998).

It has not been possible to demonstrate the transposition of Impala, other than at an extremely low rate which is incompatible with the development of a tool for insertional mutagenesis, using the niaD/Impala gene construct of the pNi160 plasmid (Langin et al., 1995) in other fungi, and more particularly *Magnaporthe grisea*. These observations suggest that the niaD/Impala construct of the pNi160 plasmid (Langin et al., 1995), and more particularly that the Impala transposon itself, are not functional in other fungi, and in particular in *M. grisea*.

Now, such a tool for creating a collection of insertion mutants in the fungus genome, and more particularly the genome of pathogenic filamentous fungi, is essential for studying their genome and for studying the function of their genes. Analyzing the functions of fungus genes is essential for discovering novel antifungal compounds which can be used for treating fungal conditions in human or animal health or for agriculture.

The present invention relates to novel polynucleotides comprising a marker gene which is functional in *Magnaporthe grisea* and which is inactivated by the insertion of an Impala transposon. These polynucleotides make it possible to demonstrate the transposition of the Impala element in fungi with a transposition rate which is compatible with the development of tools for insertional mutagenesis. A subject of the invention is also therefore methods for preparing fungus mutants by inserting an Impala transposon into their genome and methods for identifying a fungus gene associated with a phenotype of interest. Finally, the invention relates to collections of fungus insertion mutants and uses thereof.

DESCRIPTION OF THE INVENTION
Polynucleotides

The present invention therefore relates to a polynucleotide, in particular an isolated or purified polynucleotide, comprising a marker gene which is inactivated by the insertion of an Impala transposon, such that said marker gene comprises, in the direction of transcription, a promoter regulatory sequence which is functional in *Magnaporthe grisea* and which is functionally linked to the coding sequence of said marker gene.

The transformation of a fungus with a polynucleotide according to the invention and the excision of the transposon lead to the expression of the marker gene. The detection of the marker gene expression thus makes it possible to monitor the transposition events and to select the insertion mutants. The selection of the mutants can be improved by labeling the transposon with a second marker gene which is different from the first. This second marker gene makes it possible to monitor the reinsertion of the transposon into the genome of the fungus. A subject of the invention is also therefore polynucleotides as described above, in which the Impala transposon comprises a marker gene.

The marker genes used are suitable for selecting the transposition events by means of a simple screen. Any marker gene, the expression of which in a fungus can be detected with a phenotypic screen, may be used in the present invention. It is understood that the term "marker gene" also denotes chimeric genes comprising genetic elements of different origins. The marker genes of the present invention may thus combine a promoter sequence from a fungus and a coding sequence of a marker gene which is not from a fungus.

According to the invention, the expression "promoter regulatory sequence which is functional in *Magnaporthe grisea*" is intended to mean any polynucleotide which allows the expression, in *Magnaporthe grisea*, of a coding sequence to which it is functionally linked. The techniques which make it possible to determine whether a promoter sequence is functional in *Magnaporthe grisea* are known to those skilled in the art. For example, Magnaporthe may be transformed with a polynucleotide comprising, in the direction of transcription, a potential promoter sequence and a reporter gene. Monitoring the expression of the reporter gene in the fungus transformed with the polynucleotide makes it possible to determine whether this promoter sequence is functional in Magnaporthe. Any promoter sequence can thus be tested in order to determine its functionality in *Magnaporthe grisea*. The promoter regulatory sequence may be a promoter regulatory sequence of a gene from *Magnaporthe grisea*, or may originate from another fungus, and more particularly from another filamentous fungus. Advantageously, the promoter regulatory sequence which is functional in *Magnaporthe grisea* consists of the promoter regulatory sequence of a fungal nia (nitrate reductase) or gpd gene. Preferably, the promoter regulatory sequence which is functional in *Magnaporthe grisea* consists of a promoter regulatory sequence, which is functional in Magnaporthe, of the niaD (Malardier et al., 1989) or gpda gene from *Aspergillus nidulans* (Punt et al., 1990). In order to be functional in Magnaporthe, the promoter regulatory sequence of the niaD gene from *Aspergillus nidulans* is preferably longer than 337 bp, than 0.4 kb, than 0.5 kb, than 0.6 kb, than 0.7 kb, than 0.8 kb, than 0.9 kb, and more preferably longer than or equal to approximately 1 kb. In a preferred embodiment of the invention, the promoter sequence which is functional in *Magnaporthe grisea* consists of a 1.3 kb polynucleotide corresponding to the intergenic fragment between the niaD and niiA genes from *Aspergillus nidulans* (Genbank M58291; Johnstone et al., Gene 90:181–192, 1990; Punt et al., 1995). It is understood that a partial functional regulatory sequence, which is not functional per se, but the random integration of which into the genome of *Magnaporthe grisea* downstream of a *Magnaporthe grisea* promoter allows the expression of the marker gene, is not a regulatory sequence which is functional in *Magnaporthe grisea* according to the present invention.

According to a preferential embodiment of the invention, the coding sequence of the marker gene is chosen from the coding sequences of a reporter gene, the expression of which is easily measured, in particular GUS (U.S. Pat. No. 5,268,463, U.S. Pat. No. 5,599,670) or GFP (U.S. Pat. No. 5,491,084, U.S. Pat. No. 5,741,668), the coding sequences for a gene for tolerance to an antibiotic or a herbicide, such as the genes for resistance to hygromycin (hph: Punt et al., 1987), to phleomycin (ble: Drocourt, 1990) or to the herbicide bialaphos (Bar: Pall and Brunelli, 1993), or a gene for resistance to sulfonylureas (Sweigard et al., 1997). According to another preferential embodiment of the invention, the marker gene is chosen from the sequences of genes encoding enzymes, which are functional in fungi. Advantageously, the marker gene is the nitrate reductase gene. When the fragment according to the invention is integrated into an nia– fungus, the strain transformed with this construct conserves a mutant phenotype. The appearance of nia+ colonies on a minimum medium ($NaNO_3$ as the only nitrogen source) reveals the excision of the Impala transposon allowing the expression of the niaD gene. These nia+ revertants can be selected on this medium due to their dense and aerial phenotype which is different from the low flat phenotype of the nia– colonies. The use of the niaD gene as a marker requires the use of an nia– fungus. The methods for identifying nia– fungi are well known to those skilled in the art. Mention will in particular be made of the method described by Daboussi et al. (1989).

The polynucleotides of the present invention comprise a marker gene as described above which is inactivated by the insertion of an Impala transposon (Langin et al., 1995; Hua-Van et al., 1998). The Impala transposon comprises an open reading frame encoding the functional transposase bordered by inverted repeat sequences (ITRs). It inserts at a TA dinucleotide, which becomes duplicated. The excision of Impala is imprecise and most commonly leaves a three-nucleotide footprint corresponding to the left or right end of the element, in addition to the TA dinucleotide duplicated during the insertion. The point of insertion of the Impala transposon into the marker gene must therefore be chosen such that, following excision, the residual footprint does not prevent the expression of the marker gene. Preferably, the Impala transposon is inserted into the promoter sequence or into an intron of the marker gene. Several copies of Impala have been identified in *Fusarium oxysporum* and comparing their sequences has made it possible to define three subfamilies having ITRs of variable length and sequence (Hua-Van et al., 1998). In a preferred embodiment, the polynucleotides of the present invention comprise an Impala 160 transposon. The Impala 160 element comprises 1 280 bp, and it is bordered by two inverted repeat sequences of 27 bp framing an open reading frame encoding a 340 amino acid transposase (Langin et al., 1995; Genbank S75106). In a preferred embodiment, the polynucleotides of the present invention comprise the 1.3 kb promoter of the niaD gene from *Aspergillus nidulans*, functionally linked to the coding sequence of the niaD gene from *Aspergillus nidulans*, and an Impala 160 transposon inserted into the promoter of the niaD gene. In a particularly advantageous embodiment of the invention, the polynucleotides of the present invention comprise the pNiL160 plasmid. These constructs are used to transform an nia− fungus and the insertion mutants resulting from the transposition of the Impala element are selected for their nia+ phenotype on a minimum medium. In another preferred embodiment, the polynucleotides of the present invention comprise the promoter of the gpd gene from *Aspergillus nidulans*, functionally linked to the coding sequence of the hph gene for resistance to hygromycin, and an Impala 160 transposon inserted into the promoter of the gpd gene. These polynucleotides are used to transform a fungus and to select the hygromycin-resistant insertion mutants resulting from the transposition of the Impala element.

Any Impala transposon may be used in the constructs and the methods of the present invention. It is understood that the term "Impala transposon" also denotes modified Impala transposons. Among these modifications mention will be made in particular of the insertion of a marker gene or of activator sequences into the Impala transposon, or the inactivation of the transposase in order to obtain a defective Impala transposon. The construction of these modified transposons uses conventional molecular biology techniques which are well known to those skilled in the art.

The polynucleotides of the present invention are preferentially used to obtain insertion mutants of fungi. Inserting the Impala transposon into a gene generally leads to the total or partial inactivation of this gene. The use of an Impala transposon comprising activator sequences makes it possible, on the other hand, to obtain overexpression mutants. The transposon modifications thus allow the use of various methods of insertional mutagenesis (Bancroft et al., Mol. Gen. Genet. 233:449–461, 1992; Bancroft and Dean, Mol. Gen. Genet. 240:65–67, 1993; Long et al., PNAS 90:10370–10374, 1993).

The present invention therefore also relates to a polynucleotide as described above, comprising an Impala transposon into which a marker gene is inserted between the two ITRs of the transposable element without affecting the functionality of the transposase, thus making it possible to have an autonomous and labeled element. All the marker genes, the use of which is envisioned for observing the excision of the Impala transposon, may also be used for labeling said transposon in a preferred embodiment of the invention. Preferably, the marker gene is inserted downstream of the sequence encoding the transposase and upstream of the left ITR (at the NheI site). The insertion of a marker gene into the Impala transposon allows better selection of the insertion mutants. Alternatively, a truncated marker gene may be inserted into the Impala transposon. The use of a marker gene lacking a promoter makes it possible to use the polynucleotides of the present invention as a promoter trap. The use of a marker gene comprising a truncated promoter makes it possible to use the polynucleotides of the present invention as a trap for activator sequences.

Finally, the present invention relates to a polynucleotide as described above, comprising a defective Impala transposon, i.e. a transposon in which the transposase of the Impala element has been inactivated, in particular by mutation, by deletion, by insertion of a marker gene or by replacement with a marker gene. The transposition of this defective Impala element is more easily controlled in the insertional mutagenesis methods of the present invention. The construction of a defective Impala element in which the transposase is inactivated uses conventional molecular biology techniques which are known to those skilled in the art (Sambrook et al., 1989). In one embodiment of the invention, the open reading frame encoding the transposase of the Impala element is replaced with a marker gene expressed under the control of a promoter which is functional in *Magnaporthe grisea*. The coding sequence of the transposase may, for example, be replaced with the gene for resistance to hygromycin, the gene for resistance to bialaphos or the GFP gene, expressed under the control of a heterologous promoter which is functional in fungi. The defective Impala transposon conserves these insertion sequences (ITRs) and the transposition thereof may therefore be activated in trans, using a transposase placed, for example, on a replicative plasmid.

The polynucleotides of the present invention are preferably inserted into a vector. This vector can be used for transforming a host organism, such as a bacterium for example, and for replicating the polynucleotides of the present invention in this host organism. Preferably, the polynucleotides of the present invention are inserted into a vector for transforming fungi. These vectors are used for replicating or for integrating these polynucleotides into the genome of fungi. Vectors which allow the replication and the integration of polynucleotides into a host organism are well known to those skilled in the art.

Insertional Mutagenesis and Genetic Tagging

The present invention also relates to the use of the polynucleotides described above, for preparing insertion mutants of fungi and for studying the genome of these fungi.

A subject of the present invention is therefore also a method for preparing insertion mutants of fungi, comprising the following steps:

said fungus is transformed with a polynucleotide as claimed in the invention comprising a marker gene which has been inactivated by the insertion of an Impala transposon, under conditions which allow the excision of the Impala transposon of said marker gene and its reinsertion into the genome of the fungus;

the insertion mutants expressing the marker gene are identified.

It is understood that, in the methods according to the invention, the Impala transposon may be modified, and in particular modified by the insertion of a marker gene or of activation sequences. In a preferred embodiment, the Impala transposon comprises a marker gene and the insertion mutants expressing the two marker genes are selected.

Any fungus may be transformed with a polynucleotide according to the invention in order to prepare insertion mutants of this fungus. Mention will be made in particular of the ascomycetes, basidiomycetes and oomycetes. Preferably, the invention relates to the fungi of the Alternaria, Aspergillus, Botrytis, Cladosporium, Claviceps, Colletotrichum, Erysiphe, Fusarium, Mycosphaerella, Phytophthora, Pseudocercosporella, Pyrenophora, Rhynchosporium, Sclerotinia, Stagonospora, Venturia and Ustilago genera. Mention will also be made of the fungi of the Gaeumannomyces, Helminthosporium, Puccinia and Rhizoctonia genera. Preferentially, the invention relates to the fungi of the Magnaporthe and Penicillium genera. More preferentially, the invention relates to the fungi of the *Aspergillus fumigatus, Aspergillus nidulans, Botrytis cinerea, Erysiphe graminis, Mycosphaerella graminicola, Penicillium funiculosum* and *Stagonospora nodorum* species. Even more preferentially, the invention relates to *Magnaporthe grisea*.

The techniques for transforming fungi are well known to those skilled in the art. Mention will be made in particular of the transformation of protoplasts using PEG, electroporation, transformation with Agrobacterium (De Groot et al., Nature Biotechnology 16:839–842, 1998) or the methods of bombardment using a particle gun (Chaure et al., Nature Biotechnology 18:205–207, 2000).

The transformants are then screened for the expression of the marker gene in order to identify or to select the insertion mutants resulting from the transposition of the Impala element. The marker gene of the polynucleotides of the present invention makes it possible to identify or select insertion mutants by means of a phenotypic screen. By way of example, this screen may be resistance to an antibiotic, resistance to a chemical compound or the measurement of the level of expression of a reporter gene. Various marker genes are described in greater detail above. When the niaD gene is used as the marker gene in an nia− fungus, the insertion mutants are selected by virtue of their dense and aerial appearance on minimum medium containing $NaNO_3$ as the only nitrogen source.

In order to analyze the insertion mutants thus obtained, it may be advantageous to stabilize the transposon so as to avoid any new transposition. This control of new reinsertion of the transposon may be disregarded if the mutants are tested at a complement close to or below the rate of transposition of the transposition element. In order to control the excision of the transposon, a two-component system may be prepared (Hua-Van, 1998; Kempken and Kuck, 1998). The latter involves the construction of a defective Impala element in which the transposase is inactivated, in particular by mutation, by deletion or by replacement with a marker gene. In this case, the defective Impala transposon is mobilized using a transposase, the expression of which is tightly controlled, thus making it possible to stabilize the Impala element.

A subject of the present invention is therefore also a method for preparing insertion mutants of fungi, characterized in that it comprises the following steps:

said fungus is transformed with a polynucleotide comprising a marker gene which has been inactivated by the insertion of a defective Impala transposon as claimed in the invention;

the defective Impala transposon is mobilized using a transposase, the expression of which is controlled, under conditions which allow the excision of the defective Impala transposon, its reinsertion and its stabilization in the genome of the fungus;

the insertion mutants expressing the marker gene are identified.

The methods which make it possible to control the expression of a gene, such as the Impala element transposase gene, in fungi are well known to those skilled in the art. In a particular embodiment, the fungus is transformed with two polynucleotides; the first polynucleotide comprises the defective Impala transposon, while the second polynucleotide comprises the coding sequence of the Impala element transposase under the control of its own promoter or of a heterologous promoter. The coding sequence of the transposase may be placed on a replicative plasmid or on an integrative plasmid. In order to control the expression of the transposase, the latter may be placed under the control of an inducible promoter. The induction of the expression of the transposase allows the transposition of the defective Impala element and the preparation of insertion mutants, and then the transposon is stabilized when the transposase is no longer expressed. Any inducible promoter which is functional in fungi may be used in the methods of the present invention. Use may in particular be made of the promoter of the nitrate reductase gene from *Magnaporthe grisea*; specifically, this promoter allows the expression of the nia gene on a minimum medium in the presence of nitrate as the only nitrogen source, whereas the expression of this gene is totally suppressed in the presence of ammonium (Lau and Hammer, 1996). Alternatively, the transposase is, for example, placed on a replicative plasmid carrying a selection marker, this plasmid not being maintained when there is no selection pressure. In this case, the transposase may be expressed under the control of a constitutive promoter or of its own promoter. In the presence of a selection pressure, the maintaining of the replicative plasmid allows the expression of the transposase which, in turn, allows the transposition of the Impala element and the production of insertion mutants. In the absence of selection pressure allowing the replicative plasmid to be maintained, the transposase is lost and the transposon is stabilized in the mutants. The means necessary for preparing such a plasmid are well known to those skilled in the art. By way of example, the transposase may be placed in the pFAC1 replicative vector containing telomeric ends from Podospora (Barreau et al., 1998).

Insertional mutagenesis is a very effective tool for identifying novel genes of interest and for studying their function. In a preferred embodiment, a collection of insertion mutants is screened for a phenotype of interest. Any detectable phenotype may be sought in the insertion mutants of the present invention. Mention will be made in particular of phenotypes relating to the biology, physiology, development and biochemistry of fungi. Preferably, insertion mutants of pathogenic fungi are prepared and the phenotypes sought in these mutants relate to the pathogenicity of these fungi. The phenotypic screen may be based on direct observation of the fungus, on an enzymatic activity measurement, on measuring sensitivity to a fungicide or on studying the virulence of the fungus. When an insertion mutant with a phenotype of interest has been identified, the gene into which, or close to which, the Impala transposon has inserted is isolated. The gene of interest thus tagged by the insertion of the Impala element is isolated using molecular biology techniques which are well known to those skilled in the art. Among the techniques used, mention will be made in particular of the amplification techniques which allow the amplification of a polynucleotide when only the sequence of one end of the polynucleotide is known (in this case, the sequence of the transposon integrated into the genome). These techniques comprise, in particular, inverse PCR (Ochmann et al., Genetics, 120:621–623, 1988; Williams, Biotechniques 7: 762–769, 1989), vectorette PCR (Arnold and Hodgson, PCR Methods Appl. 1:39–42, 1991) and panhandle PCR (Jones and Winistorfer, PCR Methods Appl. 2:197–203, 1993). These techniques make it possible to amplify, to clone and to sequence the sequences flanking the Impala transposon in the genome of the fungus. These flanking sequences are then used to isolate the entire gene inactivated by the insertion of the transposon.

The present invention therefore also relates to a method for identifying a gene associated with a detectable phenotype in fungi, characterized in that it comprises the following steps:

insertion mutants are prepared by inserting an Impala transposon into the genome of said fungi according to one of the methods described above;

at least one insertion mutant with this detectable phenotype is selected;

the gene into which, or close to which, the Impala transposon has inserted is isolated.

Host Organisms

The present invention also relates to a host organism transformed with a polynucleotide of the present invention. According to the invention, the term "host organism" is in particular intended to mean any monocellular organism or multicellular organism, which may be a lower or higher organism, in particular chosen from bacteria and fungi. Advantageously, the bacteria are chosen from *Escherichia coli*. In a preferred embodiment, the invention relates to a fungus transformed with a polynucleotide of the present invention. Preferably, the fungus is chosen from ascomycetes, basidiomycetes and oomycetes. Preferentially, the fungi are chosen from the fungi of the Alternaria, Aspergillus, Botrytis, Cladosporium, Claviceps, Colletotrichum, Erysiphe, Fusarium, Mycosphaerella, Phytophthora, Pseudocercosporella, Pyrenophora, Rhynchosporium, Sclerotinia, Stagonospora, Venturia and Ustilago genera. Mention will also be made of the fungi of the Gaeumannomyces, Helminthosporium, Puccinia and Rhizoctonia genera. Preferentially, the fungi are chosen from Magnaporthe and Penicillium. Advantageously, the fungi are chosen from the *Aspergillus fumigatus, Aspergillus nidulans, Botrytis cinerea, Erysiphe graminis, Mycosphaerella graminicola, Penicillium funiculosum* and *Stagonospora nodorum* species. In a particularly advantageous manner, the host organism is *Magnaporthe grisea*.

The polynucleotide may be integrated into the genome of the fungus or placed on a replicative plasmid. The present invention therefore also relates to a fungus into the genome of which is integrated a polynucleotide according to the invention. The present invention also relates to insertion mutants of filamentous fungi chosen from the fungi of the Magnaporthe or Penicillium genera, into the genome of which is integrated the Impala transposon.

The reinsertion of Impala into the genome of the fungus makes it possible to generate a collection of insertion mutants of this fungus. The mutants thus obtained may be used for studying the genome of filamentous fungi.

The examples hereinafter make it possible to illustrate the present invention without, however, seeking to limit the scope thereof. All the methods or operations described below in these examples are given by way of examples and correspond to a choice, made from the various methods available to achieve the same result. This choice has no bearing on the quality of the result and, consequently, any suitable method may be used by those skilled in the art to achieve the same result. Most of the methods for engineering the DNA fragments are described in "Current Protocols in Molecular Biology" Volumes 1 and 2, Ausubel F. M. et al. or in Sambrook et al., 1989.

Figure 1:
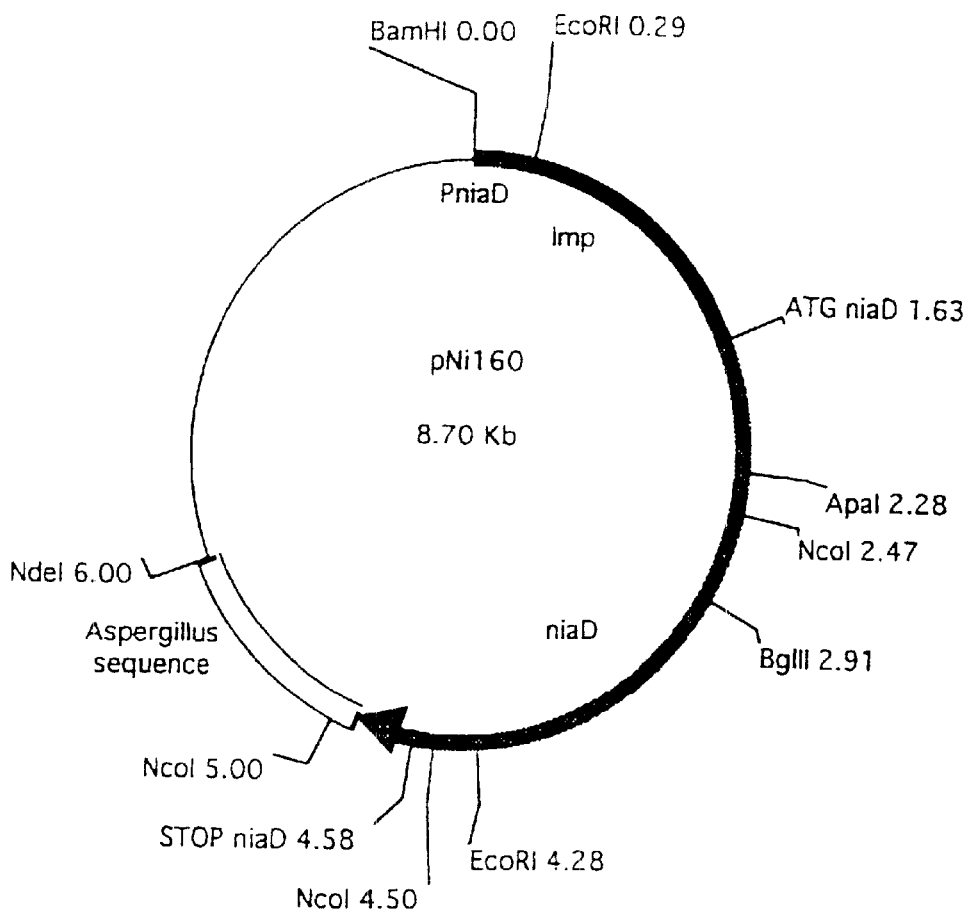
FIG. 1: Mapping of the pNi160 plasmid.

A: Analysis of the C14-1 revertant using a radioactive probe corresponding to the 2.7 kb EcoRI fragment of the niaD gene present in pAN301 (lane 1) or to the ORF encoding the Impala transposase (lane 2).

B: Analysis of the C14-1 and C14-2 revertants after having purified them by isolating nia+ monospores. The profiles of the C14-1 revertants (lanes 3 and 4) and of the C14-2 revertants (lanes 5 and 6) are compared to the profile of the C14 nia– cotransformant of origin (lanes 1 and 2). The probe used corresponds to the ORF encoding the Impala transposase.

Figure 5:
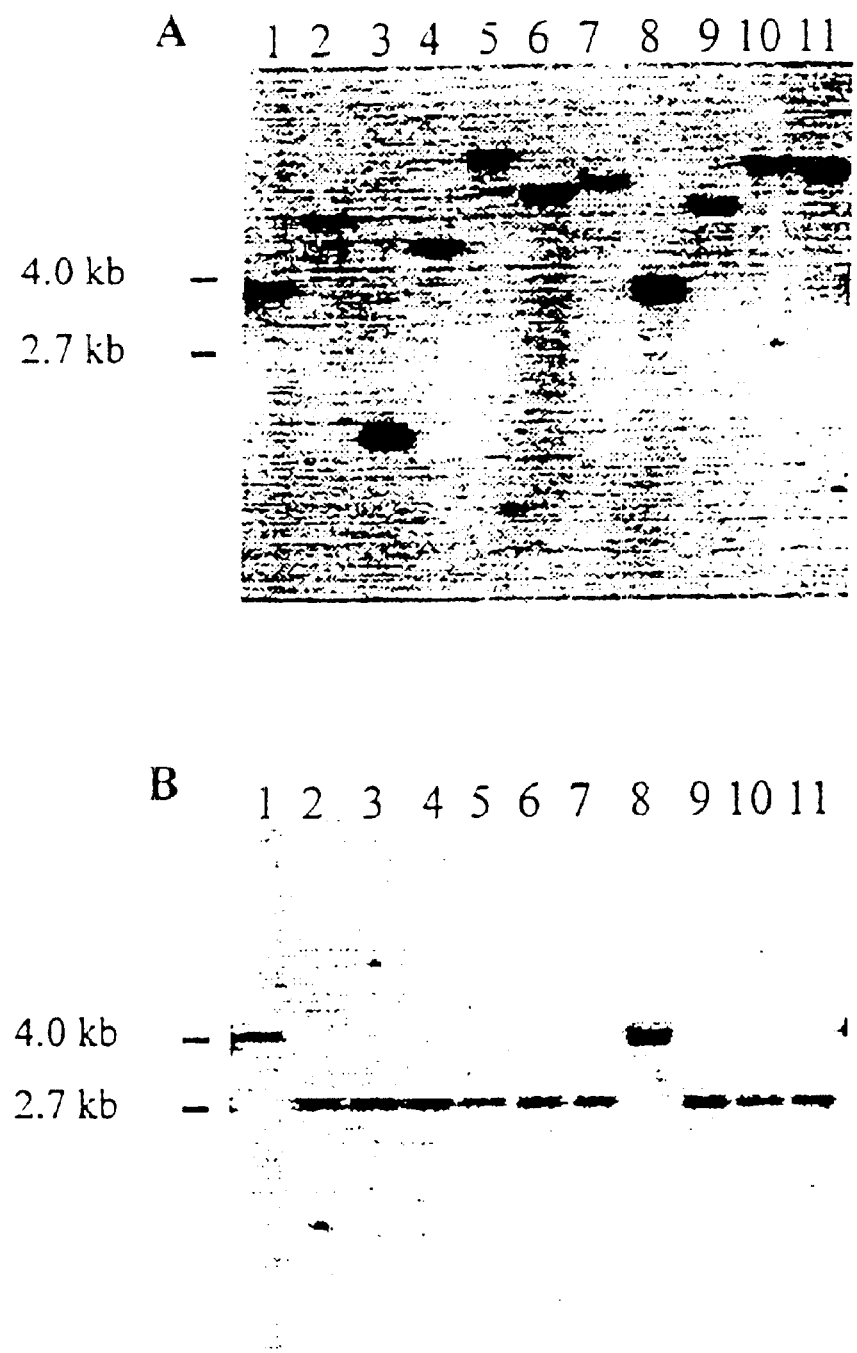

FIG. 5: Molecular analysis of nia+ revertants derived from two cotransformants carrying the pNiL160 vector. The cotransformant DNA is extracted, digested with EcoRI and loaded onto a 1% agarose gel in 1×TAE buffer (5 µg per lane). After migration and transfer onto a positive nylon membrane, the DNA fragments are revealed A: by Southern hybridization to a radioactive probe corresponding to the ORF encoding the Impala transposase; B by Southern hybridization to a radioactive probe corresponding to a 2.7 kb EcoRI fragment of the niaD gene present in pAN301. Lane 1: DNA of cotransformant 8; lanes 2 to 7: DNA of the revertants of cotransformant 8; lane 8: DNA of cotransformant 6; lanes 9 to 11: DNA of the revertants of cotransformant 6.

Figure 6:
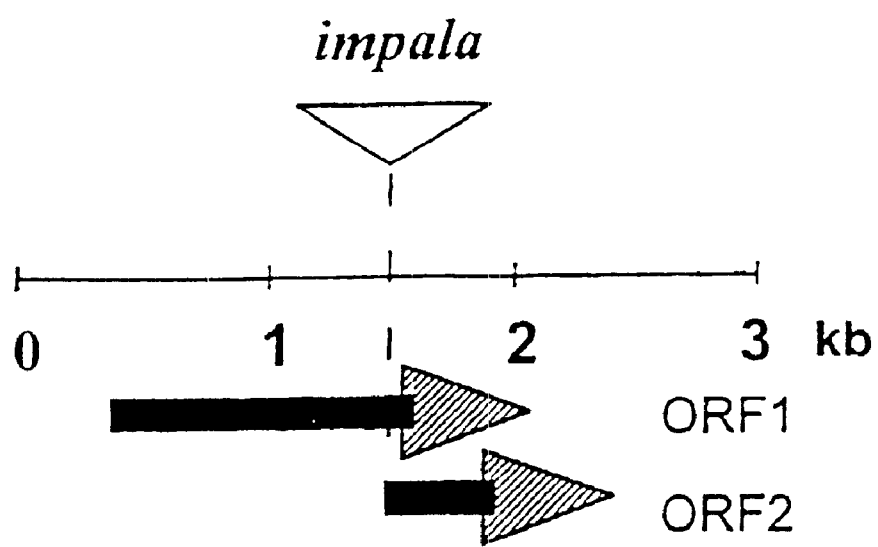

FIG. 6: Schematic diagram of the ORFs interrupted by the insertion of impala in the nonpathogenic revertant Rev77.

Figure 7:
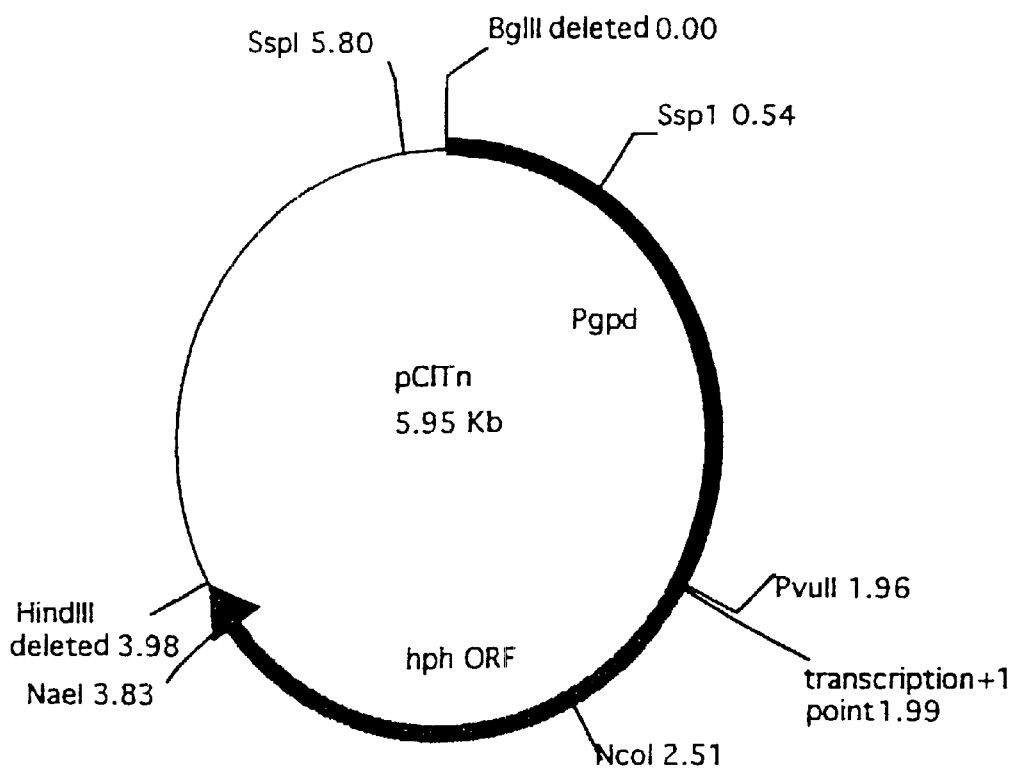

FIG. 7: Mapping of the pCITn plasmid.

Figure 8:
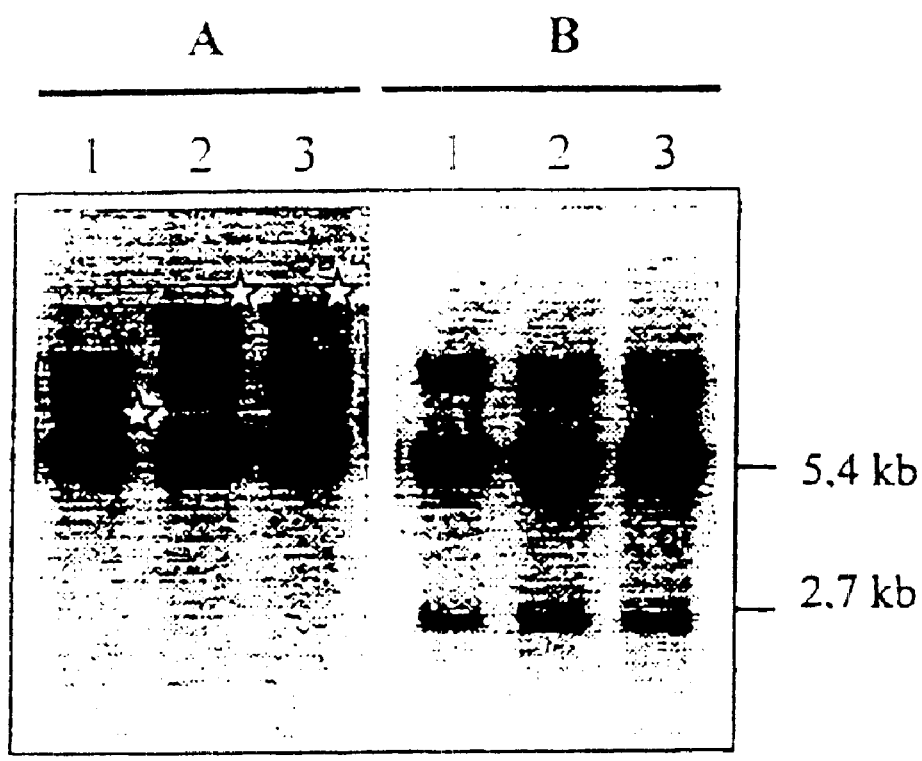

FIG. 8: Molecular analysis of nia+ revertants derived from a cotransformant carrying the pNiHYG construct. The DNA from three independent revertants (lanes 1 to 3) is extracted, digested with EcoRI and loaded onto a 1% agarose gel in 1×TAE buffer (5 µg per lane). After migration and transfer onto a positive nylon membrane, the DNA fragments are revealed A: by Southern hybridization to a radioactive probe corresponding to the ORF encoding the Impala transposase; B: by Southern hybridization to a radioactive probe corresponding to a 2.7 kb EcoRI fragment of the niaD gene present in pAN301. The position of the stars indicates the reinsertion of the transposable element.

Figure 9:
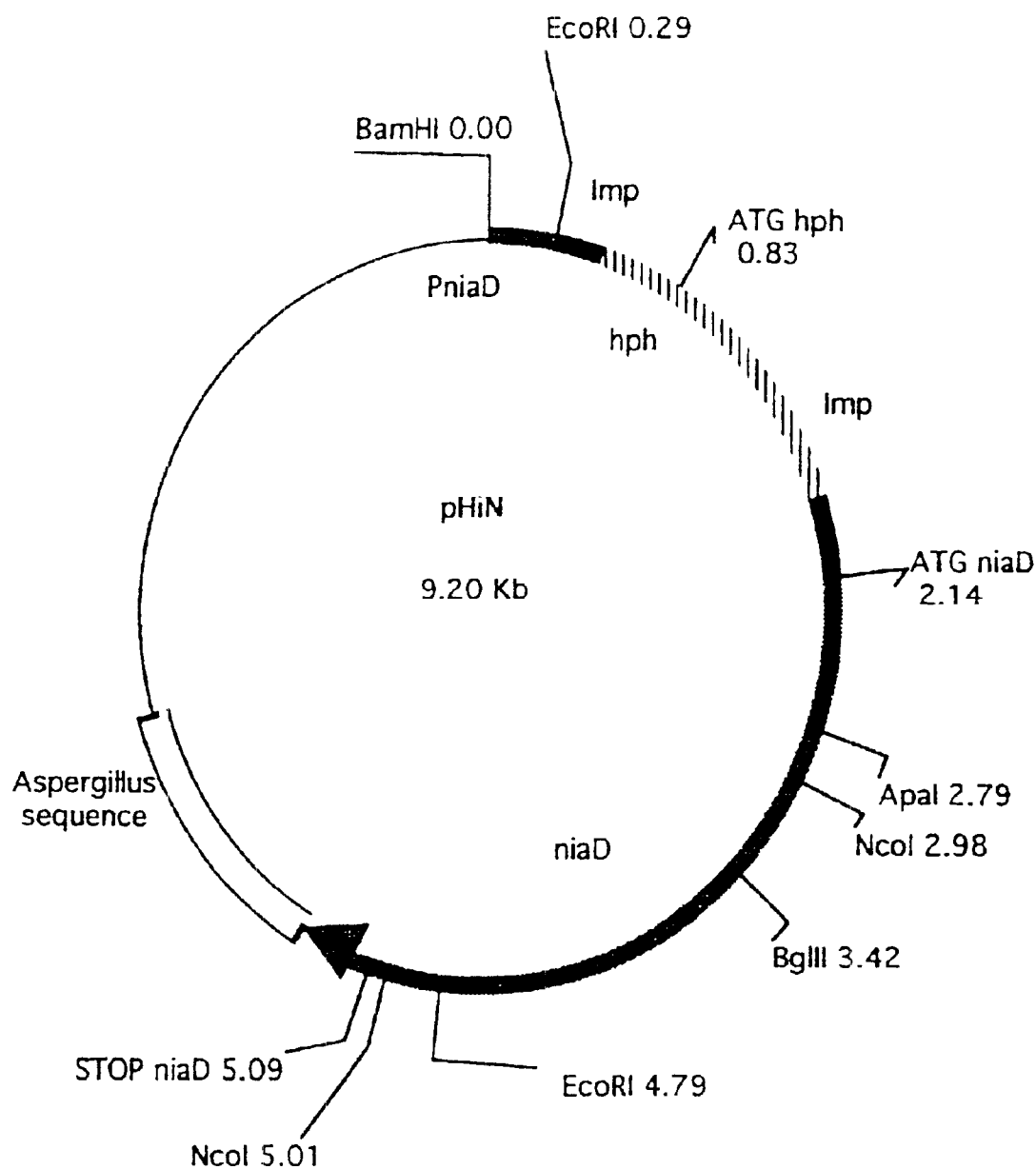

FIG. 9: Mapping of the pHIN plasmid.

Figure 10:
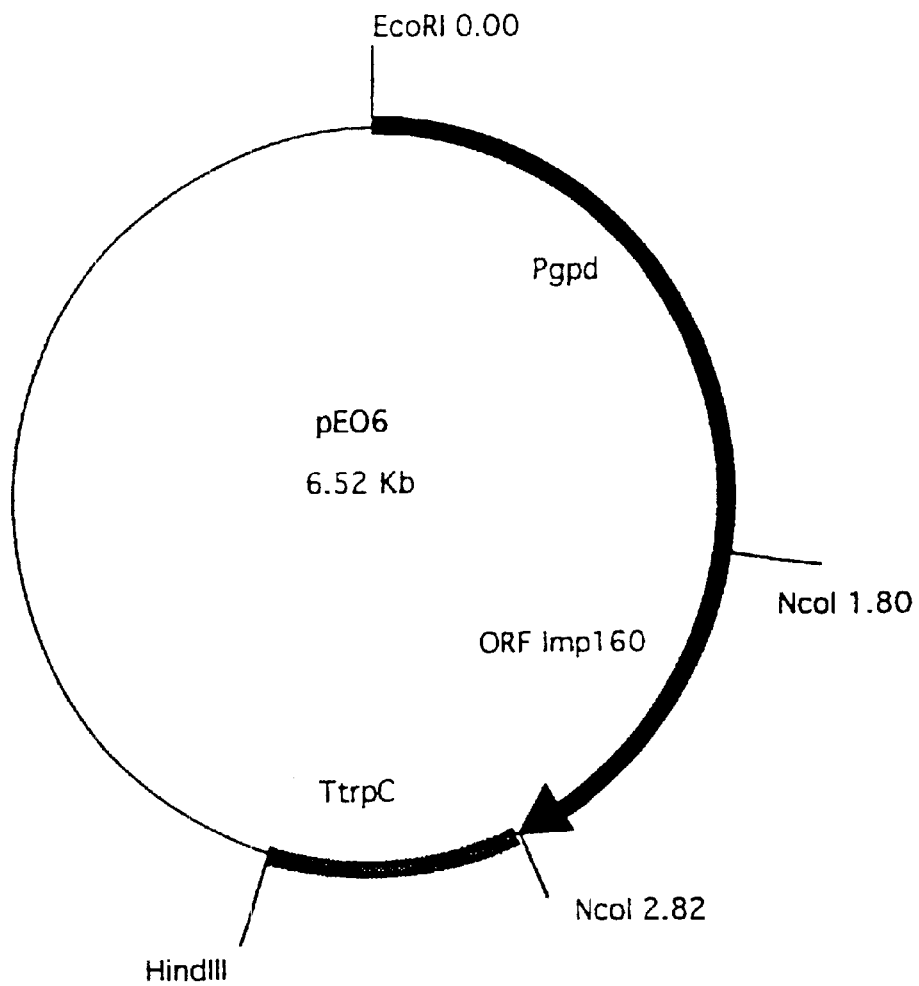

FIG. 10: Mapping of the pEO6 plasmid.

Figure 11:
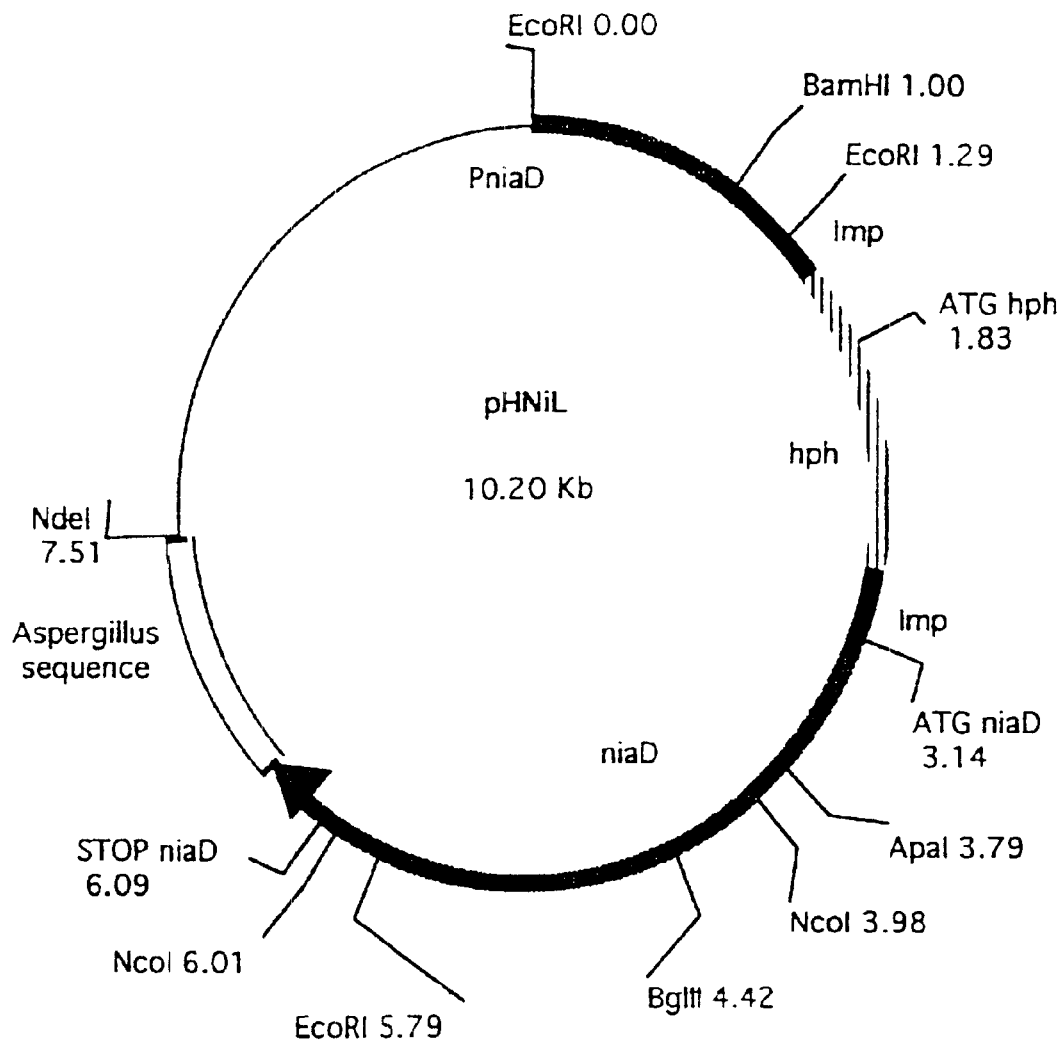

FIG. 11: Mapping of the pHNiL plasmid.

Figure 12:
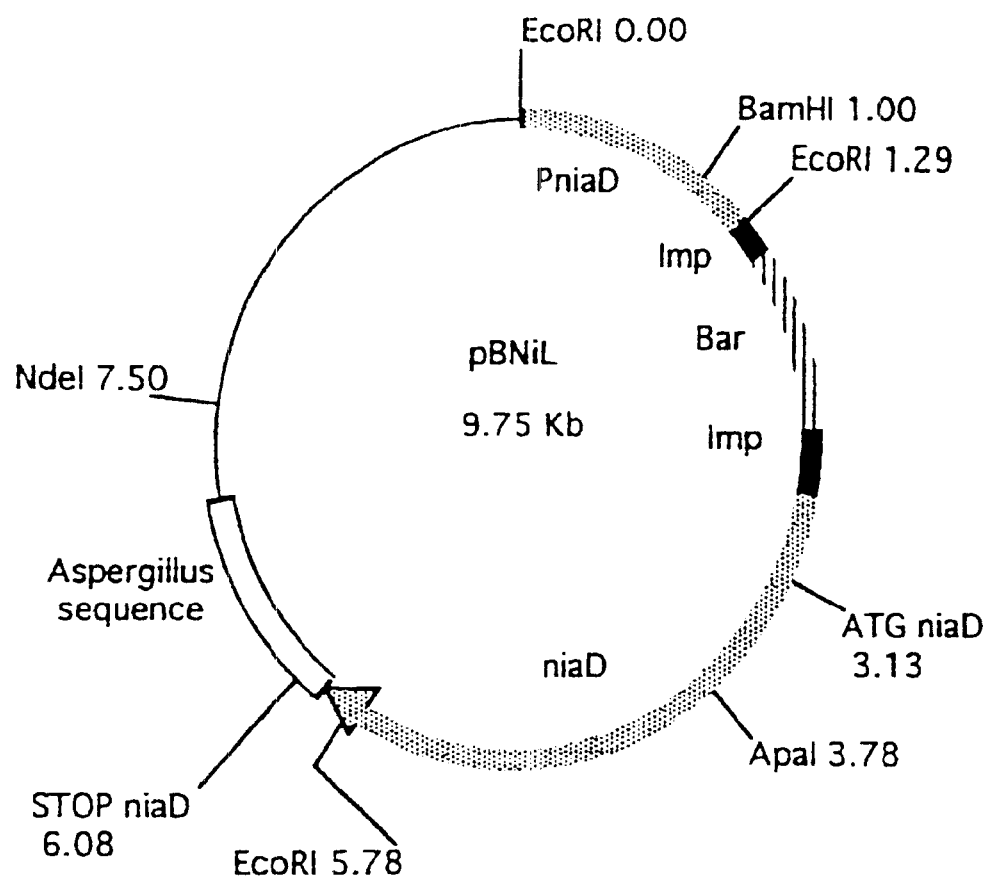

FIG. 12: Mapping of the pBNiL plasmid.

Figure 13:
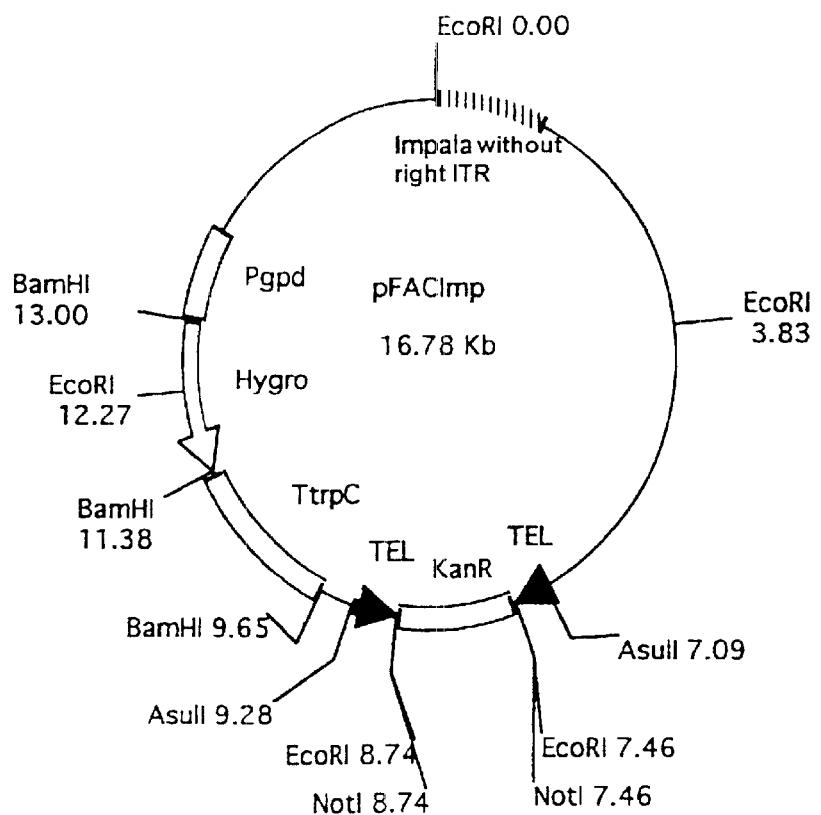

FIG. 13: Mapping of the pFACImp plasmid.

Figure 14:
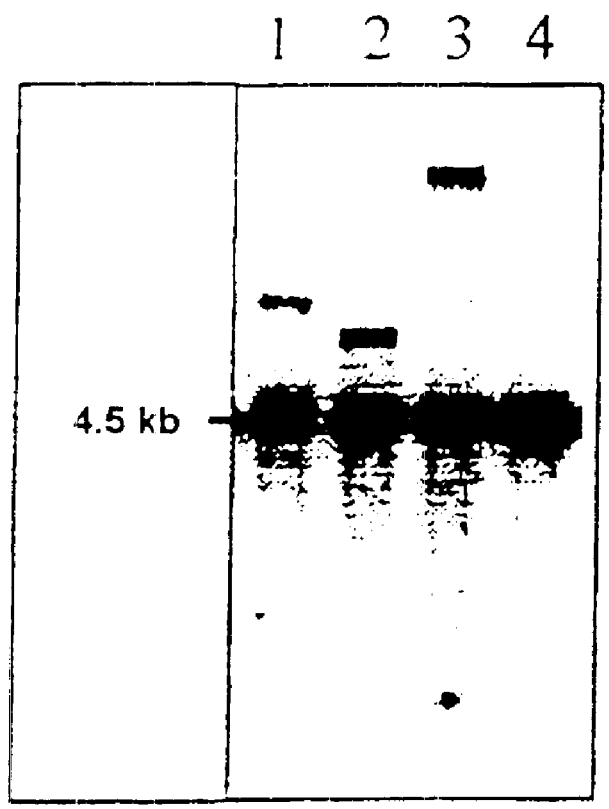

FIG. 14: Molecular analysis of nia+ revertants derived from the D1 cotransformant obtained after transformation using the two component system. The revertant DNA (lanes 1 to 4) is extracted, digested with EcoRI and loaded on to a 1% agarose gel in 1×TAE buffer (5 µg per lane). After migration and transfer onto a positive nylon membrane, the DNA fragments are revealed by Southern hybridization to a radioactive probe corresponding to a fragment amplified from the hph gene.

EXAMPLES

Example 1

Insertional Mutagenesis With an Autonomous Copy of Impala

1. Available Constructs

The pNi160 plasmid contains the Impala 160 copy integrated into the promoter region of the niaD gene from

*Aspergillus nidulans*, 10 pb from the ATG codon. Its construction derives from the transposon trap produced in the F24 strain of *Fusarium oxysporum* transformed with the pAN301 plasmid (Malardier et al., 1989) containing the nitrate reductase gene from *Aspergillus nidulans* (Daboussi et al., 1992). The selection of spontaneous mutations in the niaD gene made it possible to characterize, in the TR7 transformant, which carries a single copy of pAN301, a 1.3 kb insertion. This insertion is present in the 2.7 kb EcoRI-EcoRI region of pAN301, the effect of which is to generate a 4 kb EcoRI fragment. This fragment was cloned at the EcoRI site of pUC19, after constructing a partial genomic library and screening with the 2.7 kb EcoRI fragment from pAN301 (Langin et al., 1995). In parallel, the p11ΔNdeI plasmid was constructed from pAN301 by deleting a 7.8 kb NdeI fragment placed downstream of the niaD gene, and also a 1 kb EcoRI-BamHI fragment corresponding to the majority of the promoter of the niaD gene (Langin et al., 1990). Replacement of the 2.7 kb EcoRI fragment present in p11ΔNdeI with the 4 kb fragment comprising the 2.7 kb fragment of the nitrate reductase and the Impala 160 element made it possible to obtain the pNi160 plasmid in which the element is inserted into the promoter region of the niaD gene, which here is 0.3 kb long (FIG. 1).

2. Constructs Prepared

Figure 2:
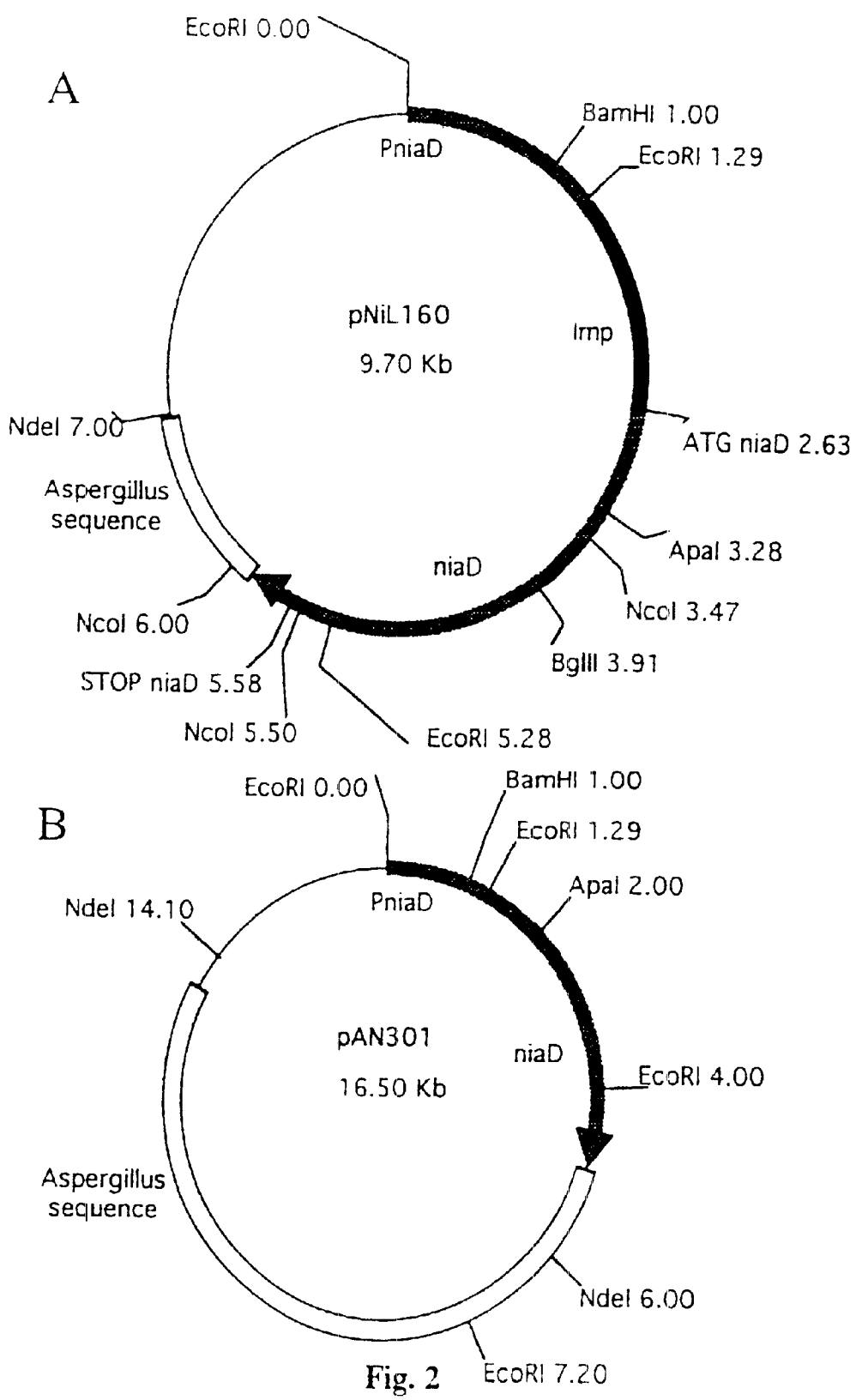
FIG. 2: Mapping of the pNiL160 plasmid (A) and of the pAN301 plasmid (B) which was used to construct it.

The pNiL160 plasmid derives from the pNi160 plasmid by the addition of a 1 kb fragment of the promoter of the niaD gene present in pAN301. To do this, the pAN301 plasmid containing 1.3 kb of niaD promoter was deleted of the 7.8 kb NdeI fragment present downstream of this gene, giving the intermediate plasmid pAN301ΔNdeI. Then, its 1 kb BamHI-ApaI fragment was replaced with a 2.3 kb BamHi-ApaI fragment, which comes from the pNi160 plasmid and contains the same portion of the niaD gene as the 1 kb fragment, plus the Impala 160 element (FIG. 2).

3. Transformation of *Magnaporthe grisea*

The G11.174 strain of *Magnaporthe grisea* has a point mutation in the nitrate reductase gene, which is responsible for its nia− phenotype. The production of this strain is described in the article Daboussi et al., 1989. It is subcultured on a riceflour-based solid medium, from which it is possible to harvest conidia from the fungus. TNKYE liquid medium prepared according to the medium B of Tanaka (Ou et al., 1985) makes it possible to harvest mycelium so as to extract the genomic DNA or to obtain protoplasts according to the protocols described by Sweigard et al., (1990) and Sweigard et al., (1992). TNK agar medium (ultra pure agarose, 8 g.l$^{-1}$) lacking yeast extract (MNO$_3$ medium) makes it possible to differentiate the nia− G11.174 strain from the nia+ G11.25 strain; the first has a low, flat and filamentous phenotype, while the second is dense and aerial.

3.1. Transformation with the pNi160 Plasmid

Figure 3:
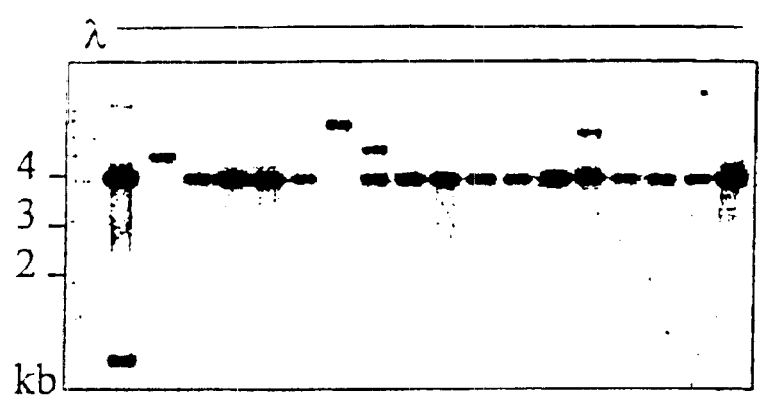
FIG. 3: Molecular analysis of the cotransformants obtained by BamHI REMI using the pNi160 and pCB1179 vectors. The cotransformant DNA is extracted, digested with EcoRI and loaded onto a 1% agarose gel in 1×TAE buffer (5 µg per lane). After migration and transfer onto a positive nylon membrane, the DNA fragments are revealed by Southern hybridization to a radioactive probe corresponding to the 2.7 kb EcoRI fragment of the niaD gene present in pAN301.
Figure 4:
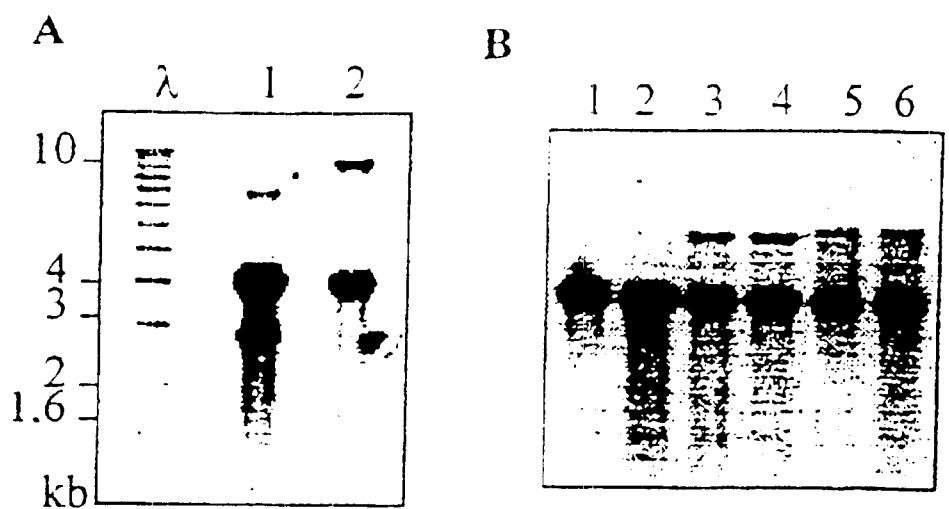
FIG. 4: Molecular analysis of the nia+ revertants C14-1 and C14-2. The revertant DNA is extracted, digested with EcoRI and loaded on to a 1% agarose gel in 1×TAE buffer (5 µg per lane). After migration and transfer onto a positive nylon membrane, the DNA fragments are revealed by Southern hybridization.

Protoplasts of the G11.174 strain were cotransformed with pNi160 plasmid (introducing Impala 160) and the pCB 1179 plasmid (Sweigard et al., 1997) conferring hygromycin resistance. The transformation method is described by Sweigard et al., 1992 and was carried out in the presence of 4 units of BamHI enzyme (REMI: restriction enzyme mediated integration; Sweigard et al., 1998) and 1 μg of each plasmid. The protoplasts are selected on a TNKYE medium in which the glucose has been replaced with sucrose (400 μg.l$^{-1}$), and supplemented with hygromycin in a proportion of 240 μg.ml$^{-1}$. In order to select the cotransformants, the colonies resistant to this antibiotic were analyzed, after extracting their genomic DNA, by amplification using the SPE5 (5'AGAACACAACCCTGCCACGG3')(SEQ ID NO:1) and SPE3 (5'TCCGGGCCGTATGCACAGAG3') (SEQ ID NO:2) primers which are specific for the Impala transposon and which generate a 573 bp amplification product. The cotransformant DNA was digested with EcoRI and analyzed by Southern blot (FIG. 3) using, as a probe, a 2.7 kb EcoRI fragment of the niaD gene (2.7 kb probe) present in pAN301 (Malardier et al., 1989). This study made it possible to select 35 cotransformants having at least one 4 kb band representing virtually the entire nia gene from *Aspergillus nidulans* introduced via pNi160. These cotransformants were cultured on riceflour-based solid medium for 10 to 14 days, and the spores were harvested in water. After counting, they were seeded onto MNO$_3$ agar medium in a proportion of 10$^5$–10$^6$ spores per dish. Experiments reconstituting this step for selecting the nia+ revertants were carried out. We thus observed that the MNO$_3$ medium makes it possible to detect nia+ colonies when 10 wild-type (G11.25) spores are mixed with 10$^6$ spores of the nia− G11.174 mutant and incubated for 14 days at 26° C. After culturing for 1 month at 26° C., only one cotransformant (cotransformant C14) made it possible to obtain two colonies (C14-1 and C14-2) with an aerial phenotype. These revertant colonies were recovered and analyzed by PCR using the C1 (5'CGCTGCGAATTCTTCAGT3')(SEQ ID NO:3) and niaX (5'CTAGACTTAGAACCTCGG3')(SEQ ID NO:4) primers framing the Impala 160 insertion site in the promoter of the niaD gene. The amplification of a 200 bp product reveals the presence of nuclei in which the excision of the transposon has taken place. In order to obtain homogeneous colonies, conidia of the C14-1 and C14-2 revertants were isolated under a binocular magnifying glass and cultured separately. The analysis thereof by Southern blot, using a probe corresponding to the ORF of Impala makes it possible to demonstrate the reinsertion of the element in the two revertants (FIG. 4). The footprint left by the excision of the transposon was sequenced after cloning the 200 bp PCR product into the pGEM-T easy vector (Promega). The footprint of the C14-1 revertant is CTGTA and that of C14-2 is CAGTA. These footprints are identical to those most commonly left by Impala when it is excised in *Fusarium oxysporum* (Langin et al., 1995). In culture on MNO$_3$ agar medium, these revertants have an intermediate phenotype which is between that of the G11.174 and G11.25 strains, suggesting that the niaD gene present in the pNi160 construct does not allow optimal complementation of the mutation of the G11.174 strain. In order to test this hypothesis, protoplasts from this strain were transformed with the pAN301 (3 μg) or pAN301ΔNdeI (3 μg) vectors containing the niaD gene under the control of 1.3 kb of promoter, and in the presence of pCB1179 (3 μg). After plating the protoplasts out and incubating at 30° C. for 10 days, on MNO$_3$ medium supplemented with hygromycin (240 μg.ml$^{-1}$) and in which the glucose has been replaced with sucrose (400 μg.l$^{-1}$), colonies with an nia+ phenotype appear. On the other hand, no complementation was observed when the p11ΔNdeI vector containing the niaD gene under the control of a 0.3 kb promoter fragment (as in the case of pNi160) was used.

These experiments demonstrate that the truncated promoter present in pNi160 is incapable of complementing the mutation of the G11.174 strain. The selection of two revertants (C14-1 and C14-2) with this construct is not due to the intrinsic activity of the 0.3 kb promoter fragment, but may be explained if it is considered that, in the C14 cotransformant, the niaD gene has inserted into a region in which it benefits from activator sequences. This suggests that p11ΔNdeI may be used with the aim of detecting activator regions in the genome of *Magnaporthe grisea*.

3.2. Transformation With pNiL160 (According to the Invention)

Protoplasts from the G11.174 strain were cotransformed with the novel construct pNiL160 (1 μg), containing the niaD gene under the control of a 1.3 kb whole promoter, and pCB1179 (1 μg), in the presence of 40 units of NdeI enzyme. The cotransformants were screened by amplification, using the SPE5 and SPE3 primers, and then seeded on rice medium for the purpose of obtaining conidia. The latter were plated out on $MNO_3$ medium (about $10^5$–$10^6$ spores per dish) in order to identify revertants. The experiment carried out on 19 cotransformants made it possible to obtain revertants in 100% of the cases; certain appear from 10 days of culture at 26° C. The number of revertants oscillates between 2 and 83 depending on the cotransformant considered. 53 revertants belonging to 8 different cotransformants were analyzed by Southern blot using a probe corresponding to the entire coding region of Impala. FIG. 5 illustrates the mobility of the impala transposon in 9 randomly chosen revertants. The percentage of Impala reinsertions in *M. grisea* taken from this experiment reaches 74%. Among these reinsertions, 95% of them are different. More particularly, cotransformants giving 100% reinsertion, all of which reinsertions are different, were identified.

These results demonstrate that the pNiL160 construct, unlike the pNi160, allows many revertants having a novel insertion of the transposon to be selected in *Magnaporthe grisea*.

Example II

Preparation of Insertion Mutants in *Magnaporthe grisea*

The Southern blot analysis of 18 nia+ revertants obtained from cotransformant 6 (CTRF6) carrying a single copy of the pNLi160 plasmid showed that 100% of them have Impala reinserted into the genome. This cotransformant was chosen to generate a collection of 350 nia+ revertants. The cotransformant is cultured for 14 days on rice medium. The spores are harvested in 3 ml of distilled water per Petri dish, filtered on sintered glass in order to eliminate the mycelial debris and plated out on NaNO3 medium in a proportion of $10^6$ spores per dish (12×12 cm format). The dishes are incubated at 26° C. The nia+ revertants appear 16 to 21 days later; they are subcultured on NaNO3 medium and cultured for 14 days, and the spores are plated out on agar-water medium (2% agarose in $H_2O$). After 8 hours at 26° C., one spore from each revertant is individually subcultured on NaNO3 medium in order to purify the revertant and to verify its nia+ phenotype.

Example III

Characterization of Insertion Mutants Carrying the Impala Transposon

The observation of 350 revertants generated from CTRF6 made it possible to detect a revertant (Rev2) exhibiting, on rice medium and NaNO3 medium, less significant growth than CTRF6, and also a dark brown coloration which is different from the gray color of the cotransformant. In order to characterize the sequences flanking the Impala insertion, 3 μg of Rev2 genomic DNA were digested with HindIII and analyzed by Inverse-PCR. After digestion, the DNA is subjected to a phenol/chloroform extraction step and then precipitated with 7.5M ammonium acetate. The pellet thus obtained is taken up in 40 μl MilliQ water. A ligation is carried out on 8 μl of digested DNA and then the DNA is subjected, as previously, to phenol/chloroform extraction and precipitated with 7.5M ammonium acetate. The DNA is taken up in 10 μl, all of which is used for a PCR step using the ImpE5' (5'GGCATTGAAAACGCGGTCCC3')(SEQ ID NO:5) and ImpE3' (5'CAGCAGCAAAACAGCTGCCC3') (SEQ ID NO:6) primers which are chosen on the sequence of the Impala transposon and which are positioned divergently. The sequencing of the IPCR product made it possible to show that the transposon is inserted into an open reading frame at a TA dinucleotide which is duplicated. Examination of the databanks using the tblastx program (Altschul et al., 1990) revealed very strong homology between this mutated sequence and a protein family involved in DNA repair, and more particularly with the MLHI protein of *Saccharomyces cerevisiae* (Prolla et al., 1994).

In parallel, in order to search for mutants of pathogeny, the 350 revertants of the collection were tested on rice leaves and barley leaves. The revertants are cultured on rice medium for 14 days. The spores produced are harvested by scraping the mycelium in the presence of 3 ml of water and then counted under a Thomas cell. The spore suspensions are adjusted to $10^5$ spores/ml and daubed, using a cotton wool bud, onto pieces of rice (cv Sariceltik) leaves and of barley (cv Express) leaves placed, in conditions of survival, on agar medium (1% agar) supplemented with Kinetin (1 ml/l of a stock solution at 2 mg/ml in ethanol). After incubation for 4 days at 26° C., the symptoms are compared to those produced by the wild-type G11.174 strain. Revertant 77 proved to be nonpathogenic. The sequences flanking the Impala insertion in this mutant were recovered by Inverse-PCR, under the conditions described above, after digesting the genomic DNA with BamHI. The recovered product again confirms the insertion of the transposon at a duplicated TA dinucleotide positioned in an open reading frame. Examination of the databanks with the sequence of this product did not demonstrate any significant homology. This product was used to probe an *M. grisea* cosmid library. A cosmid hybridizing with the amplified product was cloned, mapped and partly sequenced. It thus appears that the Impala transposon is inserted into two potential ORFs (ORF1 and ORF2) depending on the reading frame considered (FIG. 6). A SalI/NotI fragment of this cosmid was subcloned into a pCB1531 vector (pCB1531* vector) carrying the Bar gene which confers Bialophos resistance (Sweigard et al., 1997). Rev77 protoplasts were obtained and transformed with 3 μg of the pCB1531* plasmid or with 3 μg of the pCB1531 plasmid as a control, and placed on a TNKYE sucrose (400 $g.l^{-1}$) medium supplemented with Bialophos (30–40 $\mu g.ml^{-1}$). The resistant colonies are cultured on TNKYE glucose supplemented with Bialaphos (30 $\mu g.ml^{-1}$) and then left to sporulate for 14 days on rice medium. The spores are harvested, and the suspensions are calibrated at $10^5$ $spores.ml^{-1}$ and then tested with regard to their pathogeny, as described above. As expected, the transformants carrying pCB1531 remain nonpathogenic, like Rev77, whereas colonies carrying pCB1531* become pathogenic again. These results demonstrate that the Impala transposon made it possible to tag a novel gene involved in the infectious power of *M. grisea*.

Example IV

Integration of the Impala Transposon Into the Promoter of the gpd Gene

A plasmid which allows Impala to be cloned into a promoter controlling the expression of the gene for resistance to hygromycin (hph) was constructed. A BglII-HindIII double digestion of the pAN7.1 vector (Punt et al., 1987) enables the release of a 3988 bp fragment containing the entire ORF encoding the coding region of the hph gene and also the promoter of the gpd gene deleted of its first 137 base pairs and the terminator of the TrpC gene. The sticky ends of this fragment were transformed into blunt ends by the action of DNA polymerase. This fragment was subsequently ligated to a 2.5 kb PvuII fragment derived from the pBluescript SK-plasmid and carrying the origin of replication and also the gene for resistance to ampicillin. The plasmid resulting therefrom makes it possible to obtain, in *Magnaporthe grisea*, hygromycin-resistant transformants. This vector, known as pCITn (FIG. 7), has a unique PvuII site located 30 bp upstream of the transcription +1 point, into which Impala or any other transposon can be cloned.

Example V
Insertional Mutagenesis With an Autonomous and Labeled Copy

In order to obtain an autonomous element which makes it possible to select, via a phenotypic screen, the revertants in which the Impala transposon has reinserted, the gene for resistance to hygromycin was cloned between the two ITRs of the element, downstream of the stop codon of the reading frame encoding the transposase. To do this, the hygromycin-resistance cassette was recovered from the pCB1004 plasmid (Sweigard et al., 1997) by SalI digestion and the ends were made blunt by treatment with Klenow. This cassette is ligated with the pNi160 plasmid, which has been linearized at the NheI site and treated with Klenow. The resulting plasmid is digested with the BamHI and ApaI enzymes. The 2285 bp fragment containing the modified Impala transposon is recovered and ligated with the 7397 bp fragment of pAN301ΔNdeI digested with these same enzymes. This results in a 9682 bp plasmid carrying the niaD promoter, which is 1.3 kb long and into which is inserted, 8 bp upstream of the nitrate reductase initiator codon, the Impala transposon labeled with the hygromycin-resistance cassette, inserted in the direction of transcription of niaD (pNiHYG plasmid) or in the opposite direction (pNiGYH plasmid).

Protoplasts from the G11.174 strain of *M. grisea* were transformed with 3 µg of the pNiHYG plasmid or 3 µg of the pNiGYH plasmid. Selection of nia+ revertants was carried out on these transformants under the conditions already described beforehand. The analysis of three nia+ revertants of the same cotransformant, by Southern blot, shows that the Impala transposon thus labeled remains autonomous, i.e. it is capable of excising itself from the niaD gene and reinserting into the genome (FIG. 8).

Example VI
Insertional Mutagenesis With a Defective and Mobilizable Copy of Impala In order to exploit a two-component mutagenesis system it is necessary to show that the transposable element can be activated in trans. For this, the transposase is first placed under the control of a constitutive promoter. Subsequently, the stabilization of the defective element requires the use of an inducible promoter controlling the expression of the transposase or of a replicative plasmid carrying the transposase under the control of its own promoter or of a constitutive promoter. The use of the promoter of the *Magnaporthe grisea* gene encoding nitrate reductase, as an inducible promoter, appears to be particularly indicated. Lau and Hamer (1996) have shown, by Northern hybridization using a probe corresponding to a clone containing the nitrate reductase gene from *Magnaporthe grisea*, that it is expressed in the presence of nitrate as the only nitrogen source, whereas it is totally suppressed in the presence of glutamine. Placing the Impala transposase under the control of the promoter of the nia gene from *Magnaporthe grisea* should allow the enzyme to be synthesized and, consequently, the defective element to be excised under the conditions for selecting the revertants ($MNO_3$ medium) and its production to be inhibited, once the revertant has been obtained, when it is cultured on rich medium (presence of ammonium or of glutamine).

1. Available Constructs

The pHIN plasmid derives from pNi160. In that plasmid, the transposase encoded by the Impala element has been replaced with the gene for resistance to hygromycin (hph gene) under the control of the TrpC gene from *Aspergillus nidulans* (FIG. 9). The construction thereof is described in Hua-Van, 1998. The presence of the hph gene in the ITRs of the transposon makes it possible to be sure of the integration of the defective element into the genome of the revertant obtained.

The pEO6 plasmid derives from the pNOM102 plasmid after substitution of the ORF encoding β-glucuron-idase with the ORF encoding the Impala transposase obtained by PCR using primers containing an NcoI site. This plasmid allows the expression of the transposase under the control of the constitutive gpd promoter and of the TrpC terminator from *Aspergillus nidulans* (FIG. 10).

2. Constructs Prepared

The pHNiL plasmid derives from the pHIN plasmid. It was constructed by replacing the 1 kb BamHI-ApaI fragment of pAN301ΔNdeI with the 2.8 kb BamHI-ApaI fragment which comes from pHIN and introduces the defective Impala copy labeled with hph. As in pNiL160, the nitrate reductase gene (niaD) is under the control of its 1.3-kb-long promoter (FIG. 11). According to our results, it is necessary to construct this plasmid in order to select the excision of the defective element by restoring nitrate reductase activity in *Magnaporthe grisea*.

The pBNiL plasmid also contains a defective element which in this case is labeled with the Bar gene. In order to construct this vector, the BamHI/NcoI fragment of pNiL160 (2472 bp) containing the Impala transposon bordered by sequences of the niaD gene is ligated to the BamHI/AflIII fragment of pUC19 (2298 bp) carrying the origin of replication of the plasmid and the gene for resistance to ampicillin. An 891 bp XhoI/StyI fragment corresponding to part of the Impala transposase is deleted on this plasmid. The ends of the plasmid thus linearized are made blunt with Klenow and ligated with the gene for resistance to Bialaphos (Trpc promoter::Bar, 940 bp) obtained by SalI digestion of the pCB1635 plasmid (Sweigard et al., 1997) and by Klenow. The plasmid resulting therefrom is digested with BamHI and ApaI and ligated with the 7397 bp BamHI/ApaI fragment of the pAN301ΔNdeI plasmid. This results in the pBNiL plasmid in which the transposon is defective, labeled with the Bar gene and inserted into the promoter (1.3 kb) of the niaD gene (FIG. 12).

The pFACImp plasmid carries the Impala transposon in its right ITR so that it can no longer transpose but that it remains the source of the transposase. The element is excised from the pNi160 plasmid by EcoRI/NheI double digestion, the ends are made blunt with Klenow, and the fragment is cloned at the BglII site of pFAC1 (FIG. 13).

3. Use of These Plasmids in *Magnaporthe grisea*

Protoplasts from *Magnaporthe grisea* G11.174 were transformed with the pHNiL plasmid or cotransformed with the pHNiL and pEO6 plasmids. The transformation method is described by Sweigard et al. (1992) and was carried out with 1 $\mu$g of each plasmid. The protoplasts are selected on a TNKYE medium in which the glucose has been replaced with sucrose (400 $\mu g.l^{-1}$), supplemented with hygromycin in a proportion of 240 $\mu g.ml^{-1}$. The pHNiL transformants are directly selected by virtue of the presence of the resistance marker in the defective element. The cotransformants are isolated from the hygromycin-resistant colonies, after extraction of their genomic DNA, by amplification using the SPE5 primers described in IV.3. This study carried out on 12 hygromycin-resistant colonies allowed 4 colonies also carrying pEO6 to be isolated. After sporulation on riceflour-based solid medium, the spores ($10^5$–$10^6$) of these cotransformants, and also of 6 transformants carrying pHNiL, were plated out on $MNO_3$ medium in order to select nia+ revertants as described in IV.3. None of the 6 transformants carrying pHNiL gave such revertants. This shows that the defective copy of Impala cannot be mobilized by a transposon endogenous to *Magnaporthe grisea*. Among the 4 pHNiL/pEO6 cotransformants, two of them give aerial colonies (cotransformants D1 and D9). The Southern analysis of 6 revertants derived from the D1 cotransformant, after digestion of their genomic DNA with EcoRI and hybridization with an 868 by probe from the hph gene, obtained using the hyg1 (5'AGCCTGAACTCACCGCGACG3')(SEQ ID NO:7) and hyg4 (5'CGACCCTGCGCCCAAGCTGC3') (SEQ ID NO:8) primers, makes it possible to characterize the reinsertion of the defective element for 4 of them (FIG. 14). Among the latter, two revertants contain two insertions of the element. This analysis makes it possible to show that the defective element can be mobilized, in *Magnaporthe grisea*, by the Impala transposase provided in trans.

4. Other Constructs

Firstly, it involves constructing a plasmid in which the Impala transposase is under the control of the promoter of the nia gene cloned in *Magnaporthe grisea* (pNiaI). This plasmid is used in combination with pHINL or any other plasmid derived therefrom in which the niaD promoter from *Aspergillus nidulans*, inactivated by the insertion of the defective element, controls the expression of the marker genes used for selecting the revertant. In order to facilitate the selection of the cotransformants, a resistance marker, which is different from that present in the plasmid carrying the defective copy of the element, should be added to pNiaI.

Secondly, the transposase may be cloned under the control of a constitutive promoter, and more precisely under the control of the promoter of the gpdA gene, in the pFAC1 vector carrying a selection marker which is different from that present in the defective element or in the pHNiL plasmid.

References

Altschul S. F., Gish W., Miller W., Myers E. W. and Lipman D. J. (1990) Basic local alignment search tool. J. Mol. Biol. 215, 403–410

Barreau C., Iskandar M., Turcq B. and Javerzat J. P. (1998) Use of linear plasmid containing telomeres as an efficient vector for direct cloning in the filamentous fungus *Podospora anserina*. Fungal Genetics and Biology 25, 22–30

Calvi B. R., Hong T. J., Findley S. D., and Gelbart W. M. (1991) Evidence for a common evolutionary origin of inverted repeat transposons in Drosophila and plants: hobo, Activator and Tam3. Cell 66, 465–47

Capy P., Bazin C., Higuet T. and Langin T. (1998) Dynamics and evolution of transposable elements. Molecular Biology Intelligence unit. Spring-Verlag ed. Landes Biosciences. Heidelberg Doak T. G., Doerder F. P., Jahn C. L. and Herrick G. (1994) A proposed superfamily of transposase genes: transposon-like elements in ciliated protozoa and a common "D35E" motif. Proc. Natl. Acad. Sci. USA 91, 942–946

Daboussi M. J., Djeballi A., Gerninger C., Blaiseau P. L., Bouvier I., Cassan M., Lebrun M. H., Parisot D. and Brygoo Y. (1989) Transformation of seven species of filamentous fungi using the nitrate reductase gene of *Aspergillus nidulans*. Curr. Genet 14, 453–456

Daboussi M. J., Langin T. and Brygoo Y. (1992) FotI, a new family of fungal transposable elements. Mol. Gen. Genet. 232 12–16

Drocourt D., Calmels T., Reynes J. P., Baron M. and Tiraby G. (1990) Cassettes of the *Streptoalloteichus hindustanus* ble gene for transformation of lower and higher eukaryotes to phleomycin resistance. Nucleic Acids Res. 18 (13), 4009

Eickbush T. H. (1992). Transposing without ends: the non-LTR retrotransposable elements. New Biol. 4, 430–440

Finnegan D. J. (1989) Eukaryotic transposable elements and genome evolution. Trends Genet. 5, 103–107 Gems D., Johnstone I. L. and Clutterbuck A. J. (1991) An autonomously-replicating plasmid transforms *Aspergillus nidulans* at high frequency. Gene 98, 61–67

Gierl A. (1996) The En/Spm transposable element in maize. Curr Top Microbiol Immunol. 204, 145–159 Hua-Van A. (1998) Caracterisation de la famille d'éléments transposables Impala et développement d'un outil de mutagénèse insertionnelle chez le champignon phytopathogène *Fusarium oxysporum* [Characterization of the Impala transposable elements family and development of a tool for insertional mutagenesis in the phytopathogenic fungus *Fusarium oxysporum*]. Doctoratal thesis. Universite Paris 6

Hua-Van A., Hericourt F., Capy P., Daboussi M. J. and Langin T. (1998) Three highly divergent subfamilies of the Impala transposable element coexist in the genome of the fungus *Fusarium oxysporum*. Mol. Gen. Genet. 259, 354–362

Kempken F. and Kück (1998) Transposons in filamentous fungi-facts and perspectives. BioEssays 20, 652–659 Kidwell M. G. (1994) The evolutionary history of the P family of transposable elements. J. Hered. 85, 339–346 Kinsey A. J. and Helber J. (1989) Isolation of a transposable element from *Neurospora crassa*. Proc. Natl. Acad. Sci. USA 86, 1929–1933

Langin T., Daboussi M. J., Gerlingfer C. and Brygoo Y. (1990) Influence of biological parameters and gene transfer technique on transformation of *Fusarium oxysporum*. Curr. Genet. 17, 313–319

Langin T., Capy P. and Daboussi M. J. (1995) The transposable element Impala, a fungal member of the Tc1-mariner superfamily Lau G. and Hamer (1996) Regulatory genes controlling MPG1 expression and pathogenicity in the rice blast fungus *Magnaporthe grisea*. Plant Cell, 8, 771–781 Malardier L., Daboussi M. J., Julien J., Roussel F., Scazzocchio C. and Brygoo Y. (1989) Cloning of the nitrate reductase gene (niaD) of *Aspergillus nidulans* and its use for transformation of *Fusarium oxysporum*. Gene 78, 147–156

Okada N. and Hamada M. (1997) The 3' ends of tRNA-derived SINEs originated from the 3' ends of LINEs: a new example from the bovine genome. J. Mol. Evol. S52–56

Ou S. H. (1985) Blast. In: C.M. Institute (ed) Rice diseases. CAB International, Kew, UK, 109–201 Pall and Brunelli (1993) Fungal Genet Newsl. 40, 59–63 Prolla T. A, Christie D. M. and Liskay R. M. (1994) Dual requirement in yeast DNA Mismatch repair for MLH1 and PMS1, two homologs of the bacterial mutL gene. Mol. Cell. Biol 14 (1) 407–415

Punt P. J., Dingemanse M. A., Kuyvenhoven A., Soede R. D., Pouwels P. H. and van den Hondel C. A. M. J. J. (1990) Functional elements in the promoter region of the *Aspergillus nidulans* gpda gene encoding glyceraldehyde-3-phosphate dehydrogenase. Gene 93, 101–109

Punt P. J., Oliver R. P., Dingemanse M. A., Pouwels P. H. and van den Hondel C. A. M. J. J. (1997) Transformation of Aspergillus based on hygromycin B resistance marker from *Escherichia coli*. Gene 56, 117–124

Sambrook J., Fritsch E. F. and Maniatis T. (1989) Molecular cloning: a laboratory manual, second edition. Cold Spring Harbor Laboratory Press, New York Smit A. F. and Riggs A. D. (1996) Tiggers and DNA transposon fossils in the human genome. Proc. Natl. Acad. Sci. USA 93, 1443–1448

Sweigard J. A., Orbach M. J., Valent B. and Chumley F. G. (1990) A miniprep procedure for isolating genomic DNA from *Magnaporthe grisea*. Fungal Genetic Newsletter 37, 4

Sweigard J. A., Chumley F. G. and Valent B. (1992) Disruption of a *Magnaporthe grisea* cutinase gene. Mol. Gen. Genet. 232, 183–190

Sweigard J. A., Chumley F. G., Carroll A. M., Farrall L. and Valent B. (1997) A series of vectors for fungal transformation. Fungal Genet. Newsl. 44, 52–53

Sweigard J. A., Carroll A. M., Farrall L., Chumley F. G. and Valent B. (1998) *Magnaporthe grisea* pathogenicity genes obtained through insertional mutagenesis. Mol. Plant-Microbe Interact. 11, 404–412

What is claimed is:

1. An isolated polynucleotide, characterized in that it comprises a marker gene which is inactivated by the insertion of an Impala transposon, said marker gene comprising, in the direction of transcription, a promoter regulatory sequence which is functional in *Magnaporthe grisea* and which is functionally linked to the coding sequence of said marker gene.

2. The isolated polynucleotide as claimed in claim 1, characterized in that the promoter regulatory sequence is a promoter regulatory sequence of a gene from *Magnaporthe grisea*, another fungus or a filamentous fungus.

3. The polynucleotide as claimed in claim 1, characterized in that the promoter regulatory sequence consists of the promoter regulatory sequence of a fungal niaD or gpdA gene.

4. The isolated polynucleotide as claimed in claim 1, characterized in that the coding sequence of a marker gene is chosen from the coding sequences of a reporter gene, GUS, GFP, the coding sequences for a gene for tolerance to an antibiotic, the coding sequences for a gene for tolerance to an herbicide, the gene for resistance to hygromycin (hph), the gene for resistance to phleomycin (ble), the gene for resistance to the herbicide bialaphous (Bar) and a gene for resistance to sulfonylureas.

5. The isolated polynucleotide as claimed in claim 1, characterized in that the marker gene is chosen from the genes encoding enzymes which are functional in fungi, a gene encoding a nitrate reductase (niaD) or a nitrilase.

6. The polynucleotide as claimed in 1, characterized in that the Impala transposon is integrated into the promoter regulatory sequence of the polynucleotide as claimed in the invention.

7. The polynucleotide as claimed in claim 1, characterized in that the Impala transposon comprises a marker gene.

8. The polynucleotide as claimed in claim 1, characterized in that the Impala transposon is defective.

9. The isolated polynucleotide as claimed in claim 3, characterized in that the promoter regulatory sequence is a promoter regulatory sequence of the niaD gene from *Aspergillus nidulans*, which is functional in *Magnaporthe grisea*.

10. The isolated polynucleotide as claimed in claim 9, characterized in that the promoter regulatory sequence of the niaD gene from *Aspergillus nidulans* is more than 0.4 kb long.

11. The isolated polynucleotide as claimed in claim 5, characterized in that the marker gene is the nitrate reductase gene from *Aspergillus nidulans*.

12. A host organism transformed with a polynucleotide as claimed in claim 1.

13. A fungus into the genome of which is integrated a polynucleotide as claimed in claim 1.

14. The host organism as claimed in claim 12, characterized in that the host organism is a fungus.

15. The fungus as claimed in claim 13, characterized in that the marker gene is a fungal nitrate reductase gene and the fungus is nia–.

16. An insertion mutant of filamentous fungi chosen from the fungi of the Magnaporthe or Penicillium genera, into the genome of which is integrated the Impala transposon.

17. A method for preparing insertion mutants of fungi, characterized in that it comprises the following steps:
  (a) said fungus is transformed with a polynucleotide comprising a marker gene which has been inactivated by the insertion of a defective Impala transposon under conditions which allow the excision of the Impala transposon of said marker gene and its reinsertion into the genome of the fungus;
  (b) the insertion mutants expressing the marker gene are identified.

18. A method for preparing insertion mutants of fungi, characterized in that it comprises the following steps:
  (a) said fungus is transformed with a polynucleotide comprising a marker gene which has been inactivated by the insertion of a defective Impala transposon;
  (b) defective Impala transposon is mobilized using a transposase, the expression of which is controlled, under conditions which allow the excision of the defective Impala transposon, its reinsertion and its stabilization in the genome of the fungus;
  (c) the insertion mutants expressing the marker gene are identified.

* * * * *

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide primer SPE5

<400> SEQUENCE: 1
agaacacaac cctgccacgg                                                    20

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide primer SPE3

<400> SEQUENCE: 2
tccgggccgt atgcacagag                                                    20

<210> SEQ ID NO 3
<211> LENGTH: 18
<212> TYPE: DNA
<213> ORGANISM: Artificial Sequence
<220> FEATURE:
<223> OTHER INFORMATION: Oligonucleotide primer C1

<400> SEQUENCE: 3
cgctgcgaat tcttcagt                                                      18

<210> SEQ ID NO 4
<211> LENGTH: 18
<212> TYPE: DNA
<213> ORGANISM: Artificial Sequence
<220> FEATURE:
<223> OTHER INFORMATION: Oligonucleotide primer niaX

<400> SEQUENCE: 4
ctagacttag aacctcgg                                                      18

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide primer ImpE5'
```

-continued

```
<400> SEQUENCE: 5
ggcattgaaa acgcggtccc                                               20

<210> SEQ ID NO 6
<211> LENGTH: 20
<212> TYPE: DNA
<213> ORGANISM: Artificial Sequence
<220> FEATURE:
<223> OTHER INFORMATION: Oligonucleotide primer ImpE3'

<400> SEQUENCE: 6
cagcagcaaa acagctgccc                                               20

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide primer hyg1

<400> SEQUENCE: 7
agcctgaact caccgcgacg                                               20

<210> SEQ ID NO 8
<211> LENGTH: 20
<212> TYPE: DNA
<213> ORGANISM: Artificial Sequence
<220> FEATURE:
<223> OTHER INFORMATION: Oligonucleotide primer hyg4

<400> SEQUENCE: 8
cgaccctgcg cccaagctgc                                               20
```